(12) United States Patent
Robinson et al.

(10) Patent No.: US 11,051,951 B2
(45) Date of Patent: *Jul. 6, 2021

(54) EXPANDABLE INTER-BODY FUSION DEVICES AND METHODS

(71) Applicant: SPECTRUM SPINE IP HOLDINGS, LLC, Atlanta, GA (US)

(72) Inventors: James C. Robinson, Atlanta, GA (US); John E. Pendleton, Atlanta, GA (US)

(73) Assignee: Spectrum Spine IP Holdings, LLC, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/978,664

(22) Filed: May 14, 2018

(65) Prior Publication Data

US 2018/0256356 A1   Sep. 13, 2018

Related U.S. Application Data

(63) Continuation of application No. 14/216,996, filed on Mar. 17, 2014, now Pat. No. 9,987,143.

(60) Provisional application No. 61/786,612, filed on Mar. 15, 2013.

(51) Int. Cl.
   *A61F 2/44*      (2006.01)
   *A61F 2/30*      (2006.01)
   *A61F 2/46*      (2006.01)

(52) U.S. Cl.
   CPC .......... *A61F 2/447* (2013.01); *A61F 2/30744* (2013.01); *A61F 2/4611* (2013.01); *A61F 2/4684* (2013.01); *A61F 2002/30261* (2013.01); *A61F 2002/30266* (2013.01); *A61F 2002/30398* (2013.01); *A61F 2002/30507* (2013.01); *A61F 2002/30556* (2013.01); *A61F 2002/30579* (2013.01); *A61F 2002/30593* (2013.01); *A61F 2002/30904* (2013.01)

(58) Field of Classification Search
   CPC .......... A61F 2/44; A61F 2/4455; A61F 2/447; A61F 2/4465
   See application file for complete search history.

(56) References Cited

U.S. PATENT DOCUMENTS

| | | |
|---|---|---|
| 5,683,394 A | 11/1997 | Rinner |
| 5,800,550 A | 9/1998 | Sertich |
| 6,039,761 A | 3/2000 | Li et al. |
| 6,176,882 B1 | 1/2001 | Biedermann et al. |

(Continued)

FOREIGN PATENT DOCUMENTS

| | | |
|---|---|---|
| WO | 2013158294 A1 | 10/2013 |
| WO | 2016069796 A1 | 5/2016 |

OTHER PUBLICATIONS

Interventional Spine, Opticage (R) information.

*Primary Examiner* — Amy R Sipp
(74) *Attorney, Agent, or Firm* — David L. King

(57) ABSTRACT

An expandable inter-body fusion device is presented. The expandable inter-body fusion device can have a first plate, a second plate, and an insert positioned substantially therebetween the first plate and the second plate. The first plate, the second plate, and the insert define an interior cavity. Moving the insert longitudinally with respect to the first and second plates increases or decreases the distance of the first plate with respect to the second plate, effectively expanding the inter-body fusion device and increasing the volume of the interior cavity.

20 Claims, 31 Drawing Sheets

(56) References Cited

U.S. PATENT DOCUMENTS

| | | |
|---|---|---|
| 6,641,614 B1 | 11/2003 | Wagner et al. |
| 6,896,677 B1 | 5/2005 | Lin |
| 7,217,291 B2 | 5/2007 | Zucherman et al. |
| D566,276 S | 4/2008 | Blain |
| 7,722,674 B1 | 5/2010 | Grotz |
| 8,062,375 B2 | 11/2011 | Glerum et al. |
| 8,105,382 B2 | 1/2012 | Olmos et al. |
| 8,216,316 B2 | 7/2012 | Kirschman |
| 8,292,958 B1 | 10/2012 | Bruffey et al. |
| 8,343,224 B2 | 1/2013 | Lynn et al. |
| 8,366,777 B2 | 2/2013 | Matthis et al. |
| 8,382,842 B2 | 2/2013 | Greenhalgh et al. |
| 8,398,713 B2 | 3/2013 | Weiman |
| 8,568,481 B2 | 10/2013 | Olmos et al. |
| 8,845,728 B1 | 9/2014 | Abdou |
| 8,852,243 B2 | 10/2014 | Morgenstern et al. |
| 8,852,279 B2 | 10/2014 | Weiman |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum et al. |
| 8,940,049 B1 | 1/2015 | Jimenez et al. |
| 9,358,123 B2 | 6/2016 | McLuen et al. |
| 9,486,328 B2 | 11/2016 | Jimenez et al. |
| 9,492,288 B2 | 11/2016 | Wagner et al. |
| 9,522,070 B2 | 12/2016 | Flower et al. |
| 9,532,883 B2 | 1/2017 | McLuen et al. |
| 9,668,876 B2 | 6/2017 | Blain et al. |
| 9,839,527 B2 | 12/2017 | Robinson |
| 9,839,528 B2 | 12/2017 | Weiman et al. |
| 9,937,053 B2 | 4/2018 | Melkent et al. |
| 9,987,143 B2 | 6/2018 | Robinson |
| 10,098,757 B2 | 10/2018 | Logan et al. |
| 10,111,760 B2 | 10/2018 | Knapp et al. |
| 10,154,911 B2 | 12/2018 | Predick et al. |
| 10,159,583 B2 | 12/2018 | Dietzel et al. |
| 10,219,914 B2 | 3/2019 | Faulhaber |
| 2004/0087947 A1 | 5/2004 | Lim |
| 2004/0172134 A1 | 9/2004 | Berry |
| 2006/0122701 A1 | 6/2006 | Kiester |
| 2006/0129244 A1 | 6/2006 | Ensign |
| 2006/0253201 A1 | 11/2006 | McLuen |
| 2007/0270968 A1 | 11/2007 | Baynham et al. |
| 2008/0234687 A1 | 9/2008 | Schaller et al. |
| 2009/0222100 A1 | 9/2009 | Cipoletti et al. |
| 2010/0204795 A1 | 8/2010 | Greenhalgh |
| 2010/0249933 A1 | 9/2010 | Trieu |
| 2010/0292796 A1 | 11/2010 | Greenhalgh et al. |
| 2011/0282453 A1 | 11/2011 | Greenhalgh et al. |
| 2011/0307065 A1 | 12/2011 | Hsu et al. |
| 2011/0319997 A1* | 12/2011 | Glerum .................. A61F 2/442 623/17.15 |
| 2012/0029637 A1 | 2/2012 | Ragab et al. |
| 2012/0059470 A1* | 3/2012 | Weiman ................. A61F 2/447 623/17.11 |
| 2012/0071978 A1* | 3/2012 | Suedkamp ............. A61B 17/86 623/17.16 |
| 2012/0121774 A1 | 5/2012 | Marjeram et al. |
| 2012/0226357 A1 | 9/2012 | Varela |
| 2012/0232552 A1 | 9/2012 | Morgenstern Lopez |
| 2012/0310349 A1 | 12/2012 | Gordon et al. |
| 2013/0023994 A1 | 1/2013 | Glerum |
| 2013/0085572 A1 | 4/2013 | Glerum et al. |
| 2013/0103153 A1 | 4/2013 | Blackwell et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor |
| 2013/0211526 A1 | 8/2013 | Alheidt et al. |
| 2014/0121774 A1 | 5/2014 | Glerum et al. |
| 2014/0296984 A1 | 10/2014 | Etminan |
| 2015/0012097 A1 | 1/2015 | Ibarra et al. |
| 2015/0012098 A1 | 1/2015 | Eastlack et al. |
| 2015/0012101 A1 | 1/2015 | Glerum et al. |
| 2015/0073553 A1 | 3/2015 | Barreiro et al. |
| 2015/0112438 A1 | 4/2015 | McLean |
| 2016/0166396 A1 | 6/2016 | McClintock |
| 2017/0042695 A1 | 2/2017 | Foley et al. |
| 2017/0105844 A1 | 4/2017 | Kuyler et al. |
| 2017/0333198 A1 | 11/2017 | Robinson |
| 2018/0318101 A1 | 11/2018 | Engstrom |

* cited by examiner

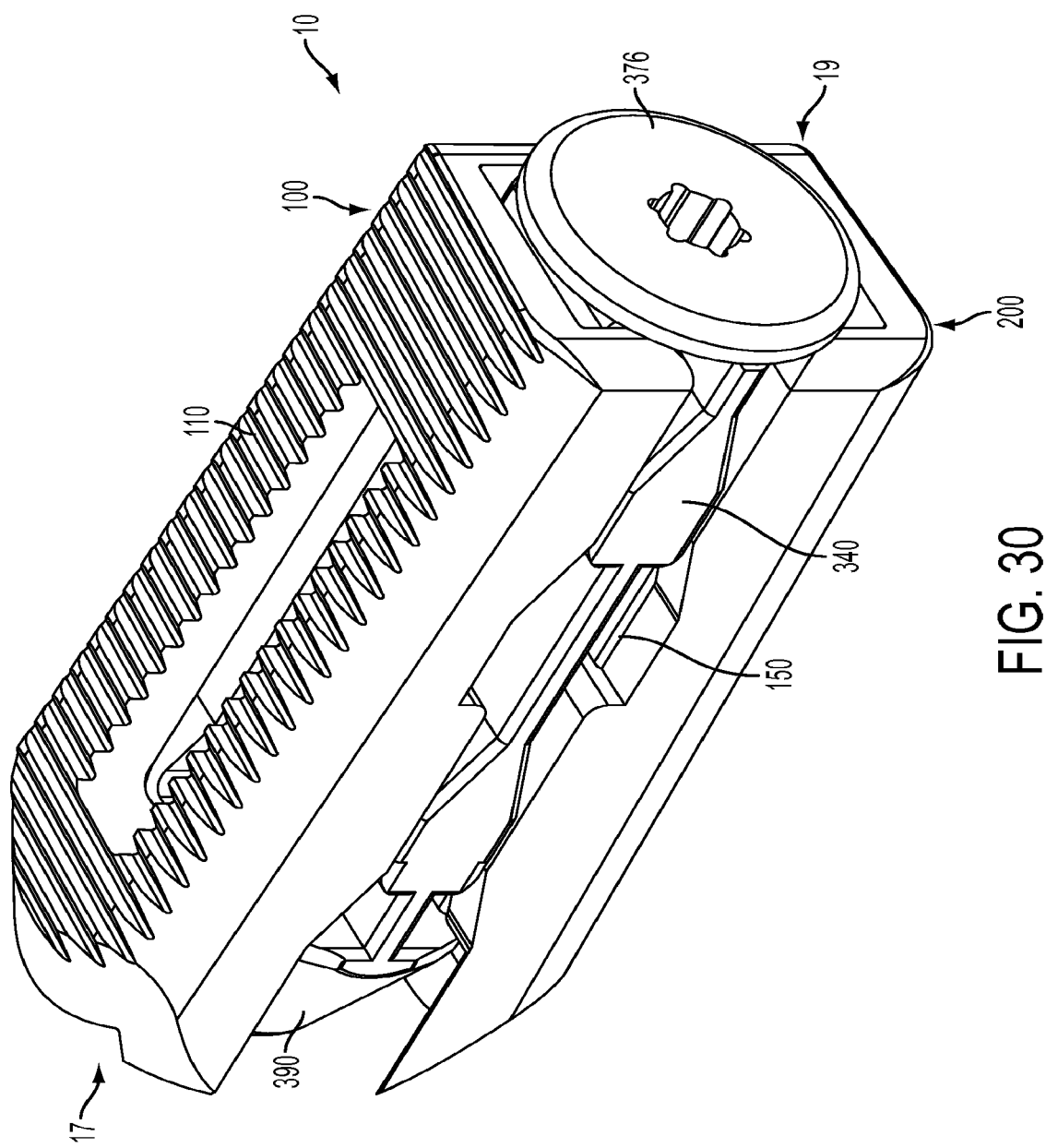

EXPANDABLE INTER-BODY FUSION DEVICES AND METHODS

CROSS-REFERENCE TO RELATED APPLICATIONS

This application is a continuation of U.S. application Ser. No. 14/216,996, filed Mar. 17, 2014, which claims the benefit of priority of U.S. Provisional Application No. 61/786,612, filed Mar. 15, 2013, which is incorporated in its entirety by this reference.

FIELD OF THE INVENTION

This invention relates generally to spinal surgery, and more particularly to devices and methods for stabilization of the spine in association with placement of an expandable inter-body construct for inter-body fusion or the like.

BACKGROUND OF THE INVENTION

Damage or disease that affects the spinal disc within an individual's spinal column may lead to neurologic impairment with possible permanent damage to the surrounding tissue. Maintaining proper anatomic spacing and lordosis within the spine is critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. Some of the known procedures for introducing spinal implants comprise Anterior Lumbar Inter-body Fusion ("ALIF"), Lateral Lumbar Inter-body Fusion ("LLIF"), Posterior Lumbar Inter-body Fusion ("PLIF"), Oblique Lumbar Inter-body Fusion ("OLIF"), Direct Lateral Fusion ("DLIF"), Transforaminal Lumbar Interbody Fusion ("TLIF"), and the like. A need remains for a multipurpose instrument to be used to implant a spacer type of implant that allows the surgeon to minimize the size of the surgical incision, facilitate the operative technique and decrease patient morbidity.

SUMMARY

Presented herein is an expandable inter-body fusion device, or implant, for use in spinal surgery. In one aspect, the expandable inter-body fusion device comprises a first plate, a second plate, and an insert positioned substantially therebetween the first plate and the second plate. The first plate, the second plate, and the insert define an interior cavity. In one aspect, moving the insert longitudinally with respect to the first and second plates increases or decreases the distance between the first plate relative to the second plate, effectively expanding the inter-body fusion device and increasing the volume of the interior cavity.

It is contemplated that this technology can be used for a variety of implants used for a variety of spinal procedures. These procedures include, but are not limited to OLIF (anterior or posterior), DLIF, PLIF, TLIF, ALIF, and LLIF. So, depending upon the procedure and point of insertion for the implant, the geometry of the implant can differ.

In an exemplified aspect, at least one of the first plate and the second plate define at least one graft window that is in communication with the interior cavity.

Also presented herein is a method of using an expandable inter-body fusion device during an inter-body fusion procedure. In one aspect, the method comprises accessing the desired disc space, choosing the correct insert size with the appropriate height and angle, inserting the expandable inter-body fusion device into the desired area in the disc space, expanding the expandable inter-body fusion device from the first non-expanded position to the second expanded position, and securing the insert to the first and second plates. An additional step of packing the interior cavity via the aperture in the trailing end of the expandable inter-body fusion device with bone fusion material either prior to or after expansion is also contemplated.

Related methods of operation are also provided. Other apparatuses, methods, systems, features, and advantages of the expandable inter-body fusion device and the method of its use will be or become apparent to one with skill in the art upon examination of the following figures and detailed description. It is intended that all such additional apparatuses, methods, systems, features, and advantages be included within this description, be within the scope of the expandable inter-body fusion device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 30 is a perspective view of the expandable inter-body fusion device of FIG. 26 in the second expanded position.

DESCRIPTION OF THE INVENTION

Figure 1:
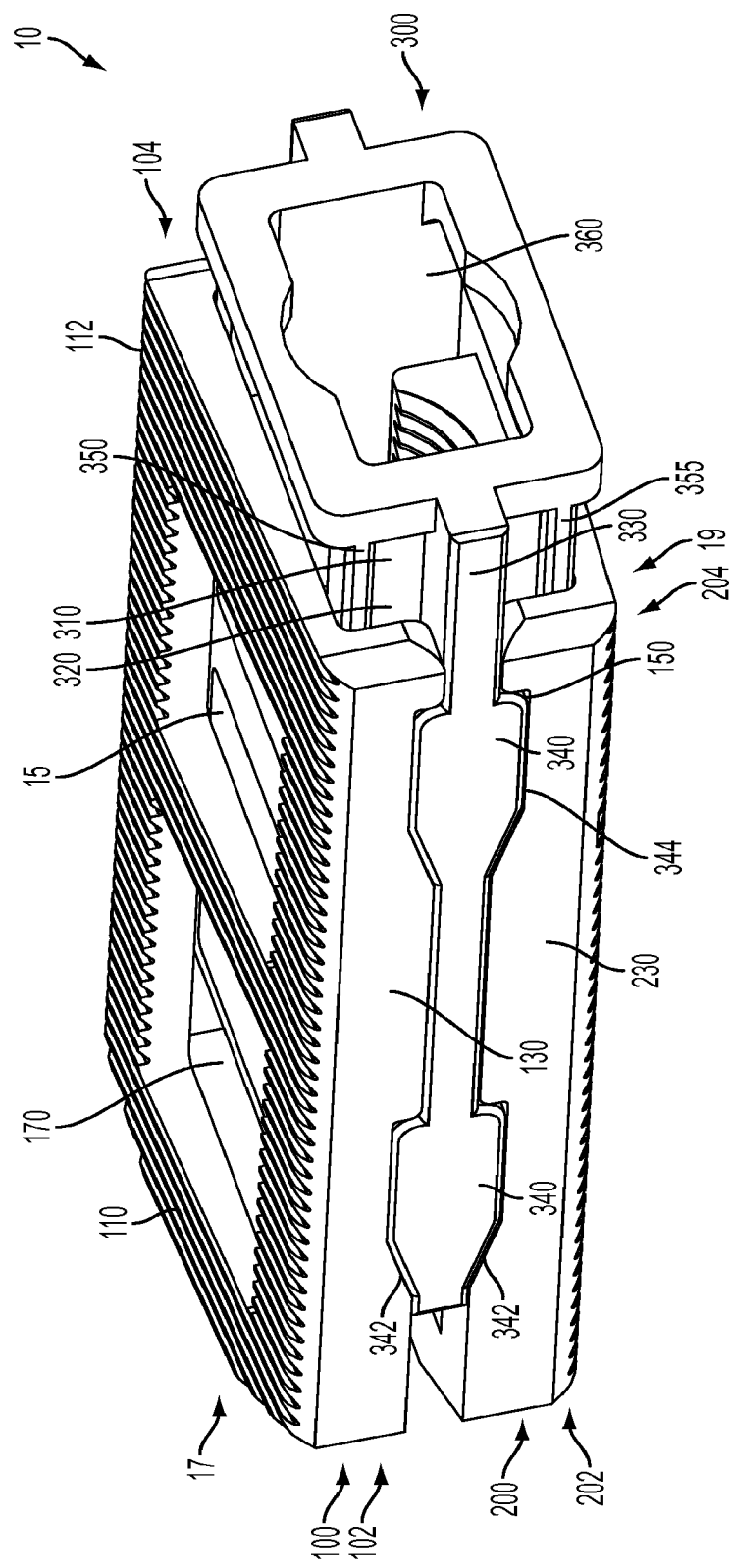
FIG. 1 is a perspective view of one aspect of an expandable inter-body fusion device that is expandable by moving an insert toward a leading end of the device, in a first unexpanded position.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

In one aspect, presented herein is an expandable inter-body fusion device 10 for use in spinal surgery, such as, but not limited to, ALIF, OLIF, TLIF, LLIF, PLIF, and DLIF procedures.

Figure 2:
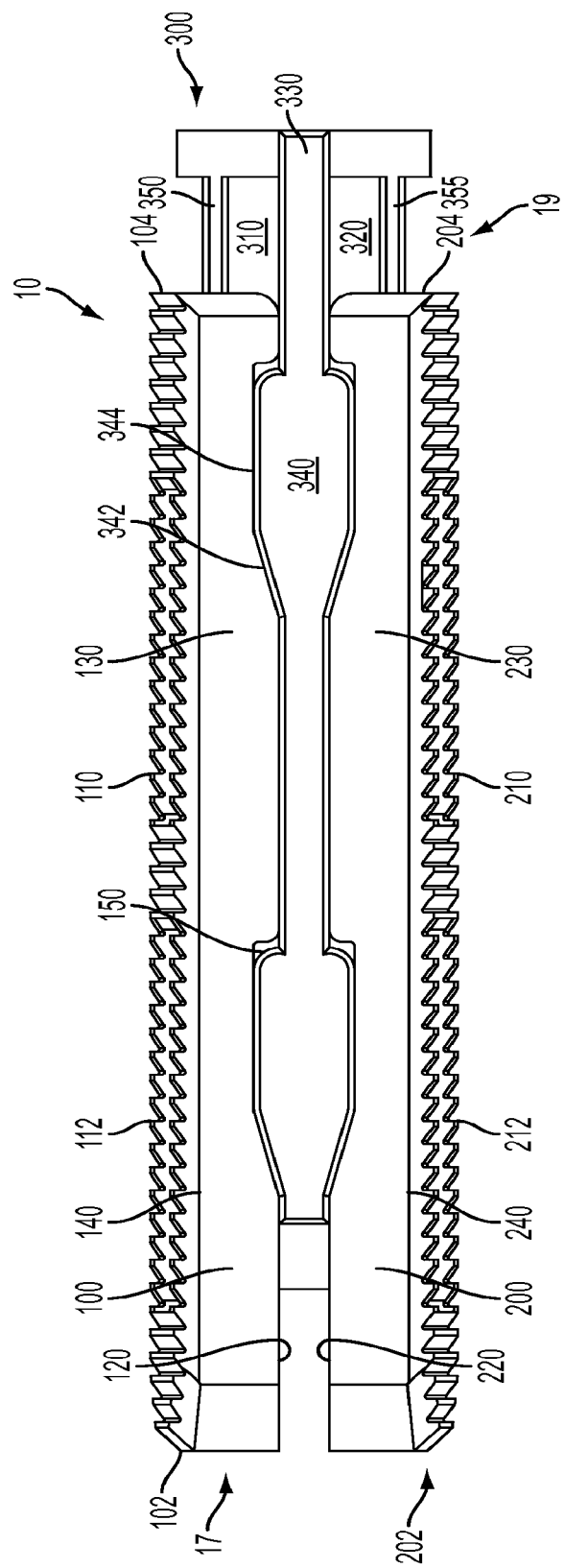
FIG. 2 is a side elevational view of the expandable inter-body fusion device of FIG. 1, illustrating an aspect that is not substantially angled longitudinally, in the first unexpanded position.
Figure 3:
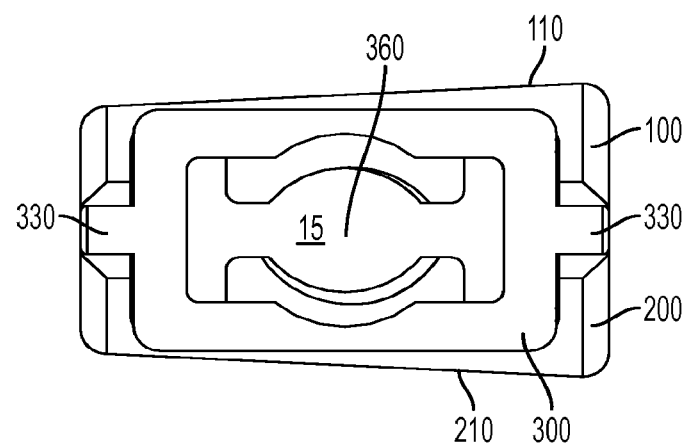
FIG. 3 is a trailing end elevational view of the expandable inter-body fusion device FIG. 1, illustrating an aspect that is angled transversely.

In one aspect and as illustrated in FIGS. 1-3, the expandable inter-body fusion device 10 comprises a first plate 100, a second plate 200, and an insert 300 positioned substantially therebetween the first plate 100 and the second plate 200. The first plate has a leading edge 102, a trailing edge 104, an upper bone contact surface 110 and an opposed first plate inner surface 120. The second plate 200 has a leading edge 202, a trailing edge 204, a lower bone contact surface 210 and an opposed second plate inner surface 220. The first plate 100, the second plate 200, and the insert 300 define an interior cavity 15. The expandable inter-body fusion device 10 has a leading end 17 and a trailing end 19. In one aspect, moving the insert longitudinally with respect to the first and second plates (that is, either toward the leading end or toward the trailing end of the device) can increase the distance between the first plate 100 relative to the second plate 200, effectively expanding the inter-body fusion device and increasing the volume of the interior cavity 15.

Figure 6:
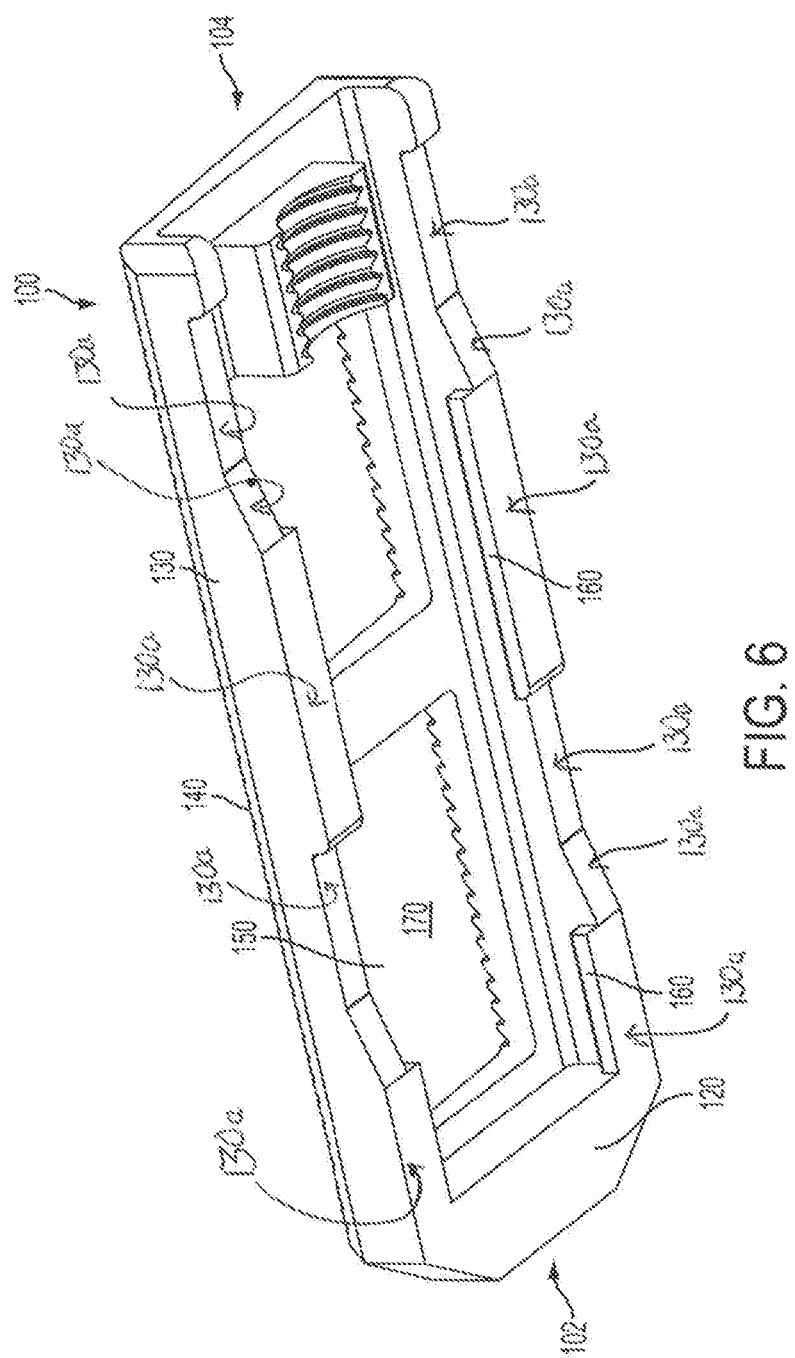
FIG. 6 is a bottom perspective view of a first plate of the expandable inter-body fusion device of FIG. 1.
Figure 7:
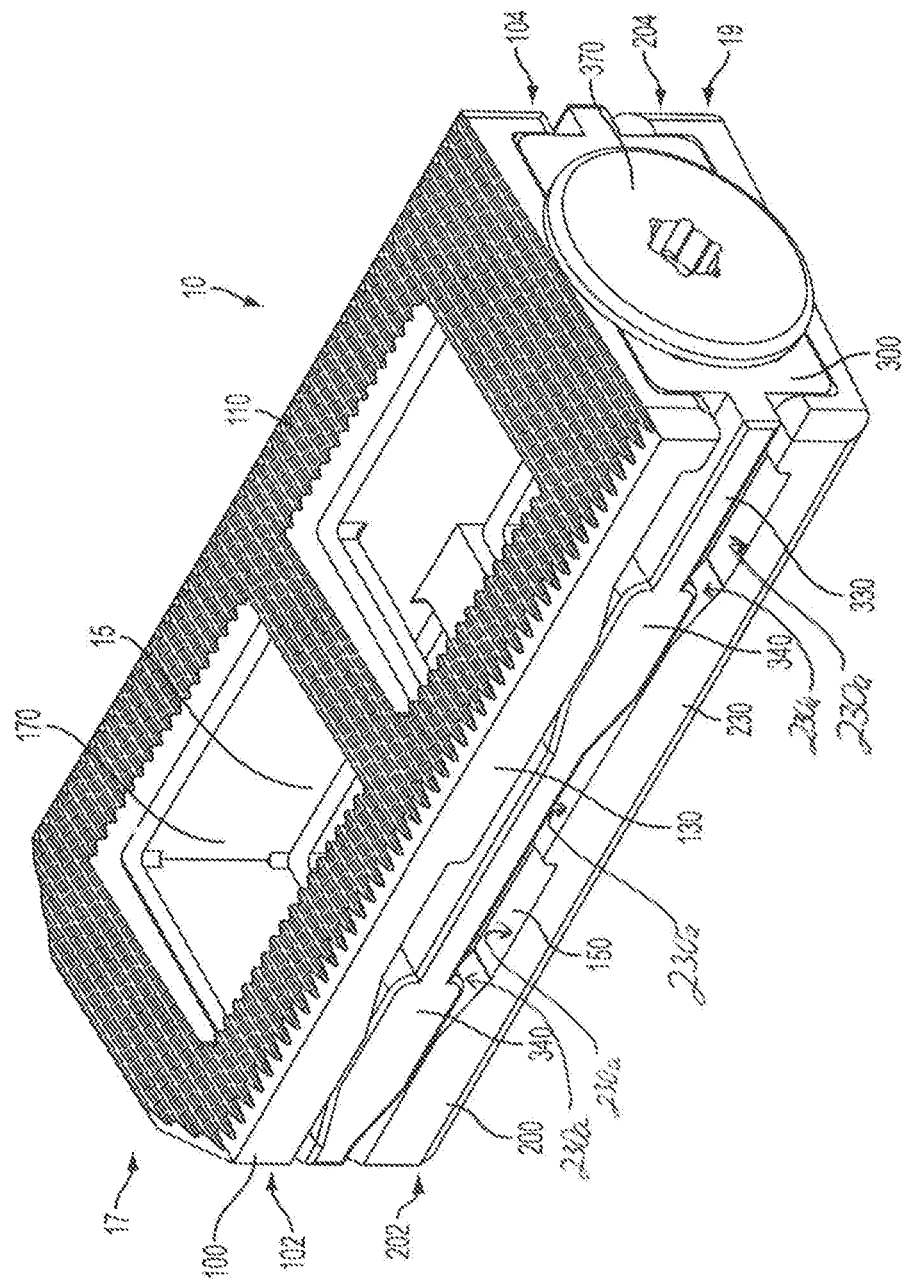
FIG. 7 is a perspective view of the expandable inter-body fusion device of FIG. 1 in a second expanded position.
Figure 8:
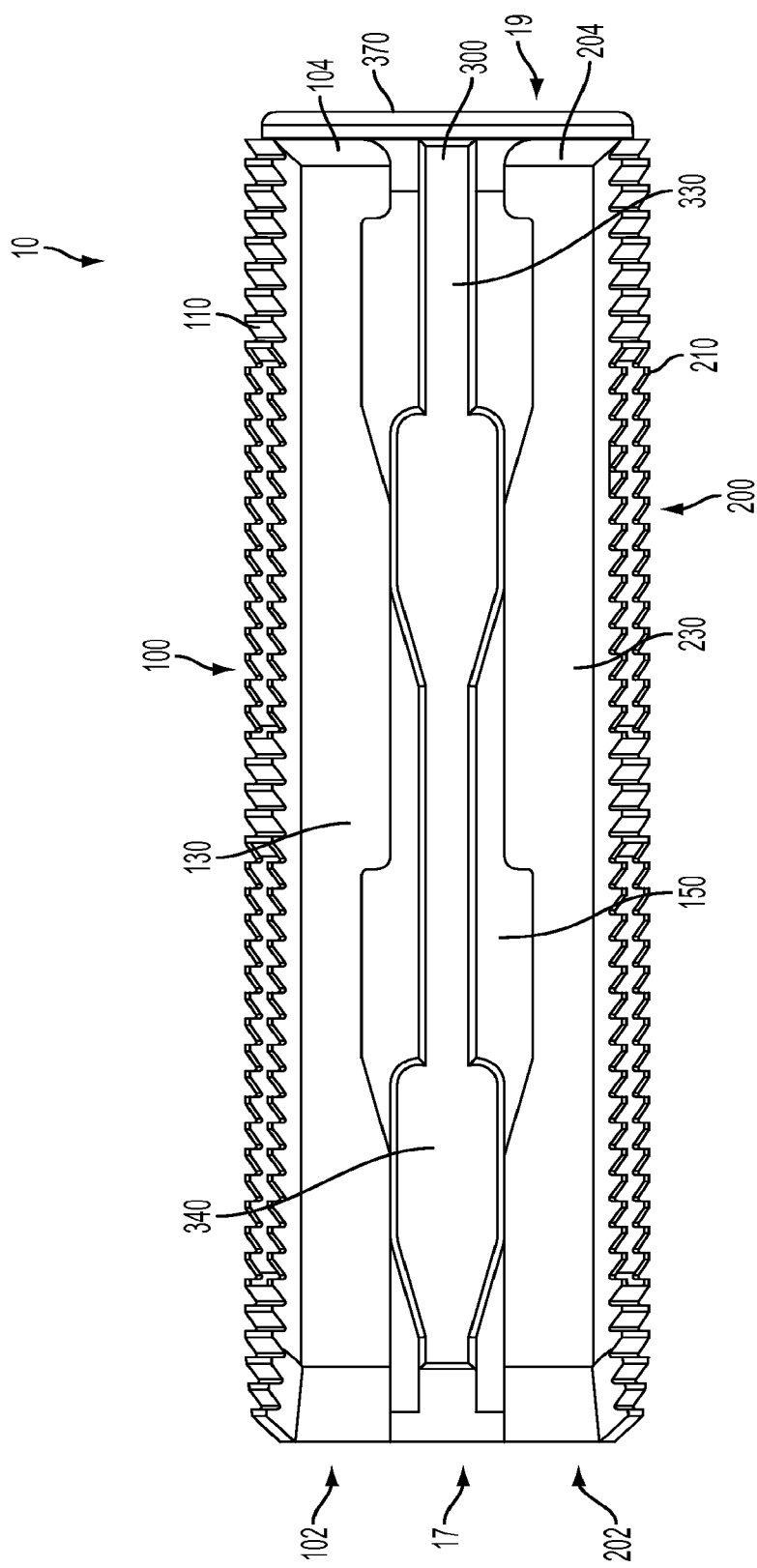
FIG. 8 is a side elevational view of the expandable inter-body fusion device of FIG. 1 in the second expanded position.
Figure 9:
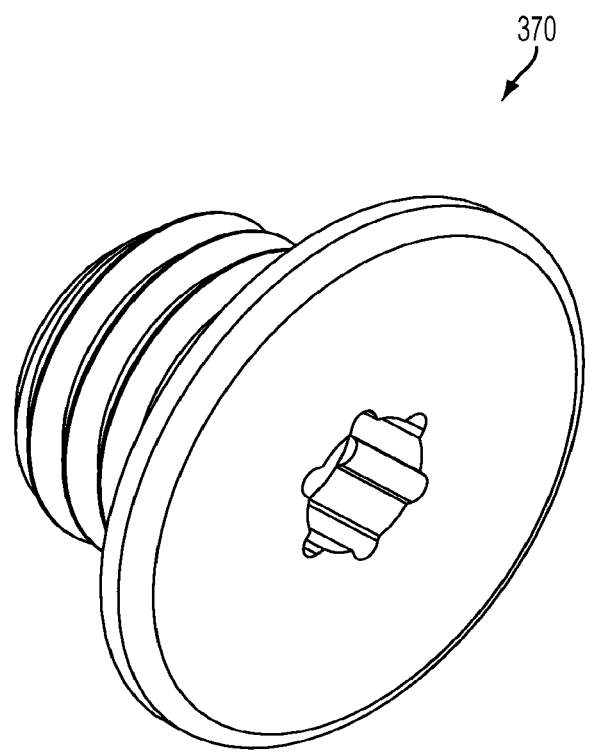
FIG. 9 is a perspective view of a threaded endcap for use with the expandable inter-body fusion device of FIG. 1.
Figure 10:
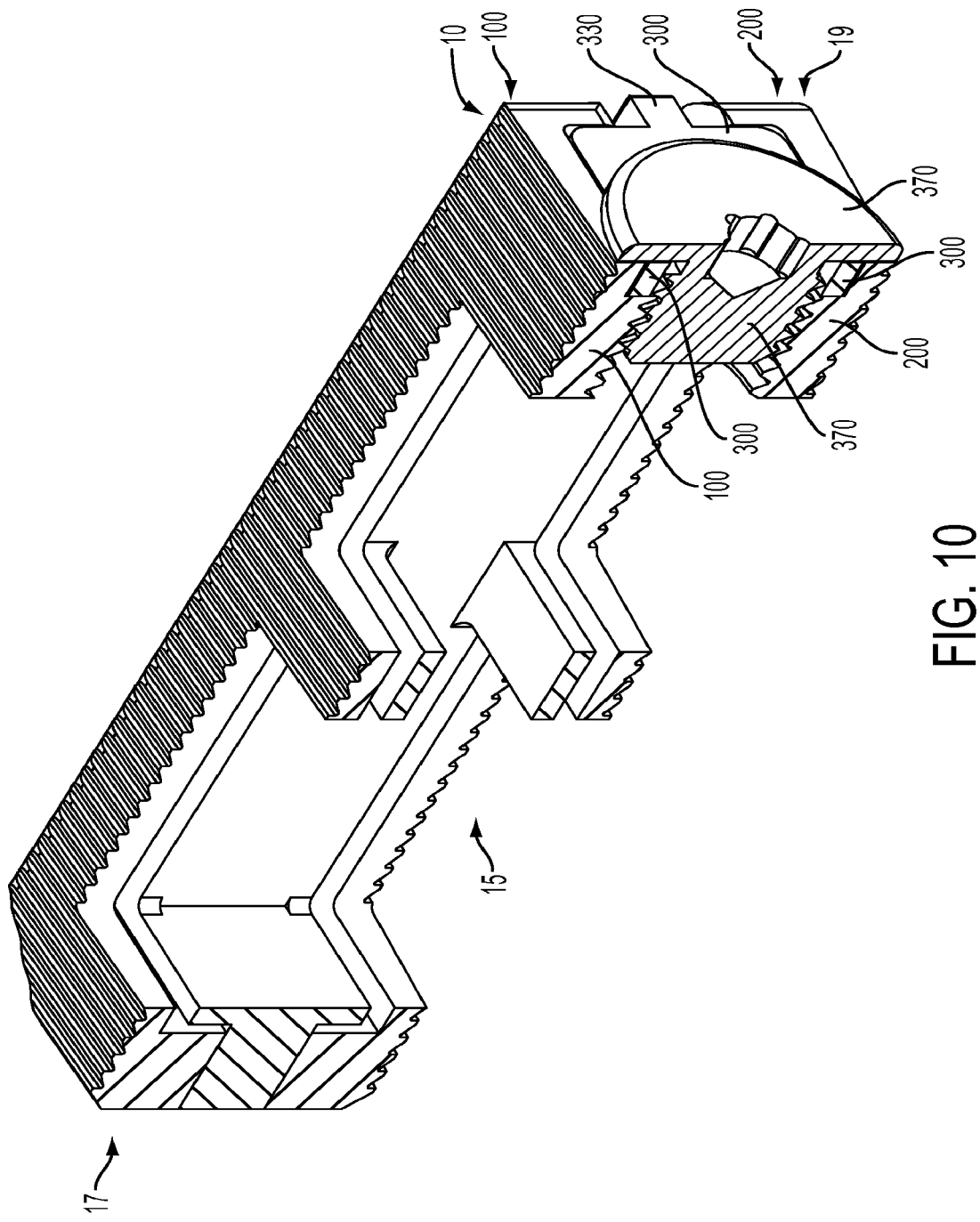
FIG. 10 is a cutaway perspective view of the expandable inter-body fusion device of FIG. 1 in the second expanded position, cut substantially along the longitudinal axis and having the endcap of FIG. 9.

At least one of the first plate 100 and the second plate 200 has at least one longitudinal sidewall 130, 230 extending substantially from the respective inner surface 120, 220. In one aspect, the at least one longitudinal sidewall 130, 230 comprises a plurality of longitudinal sidewalls. For example, the longitudinal sidewall can comprise two longitudinal sidewalls. In another aspect, the longitudinal sidewall(s) can be positioned substantially near a peripheral edge 140, 240 of the first and/or second plate. The longitudinal sidewall 130 of the first plate 100 defines a lowermost sidewall surface 130a contoured in a vertical direction, as best shown in FIG. 6. The longitudinal sidewall 230 of the second plate 200 an uppermost sidewall surface 230 contoured in the vertical direction, as best shown in FIG. 7.

Figure 4:
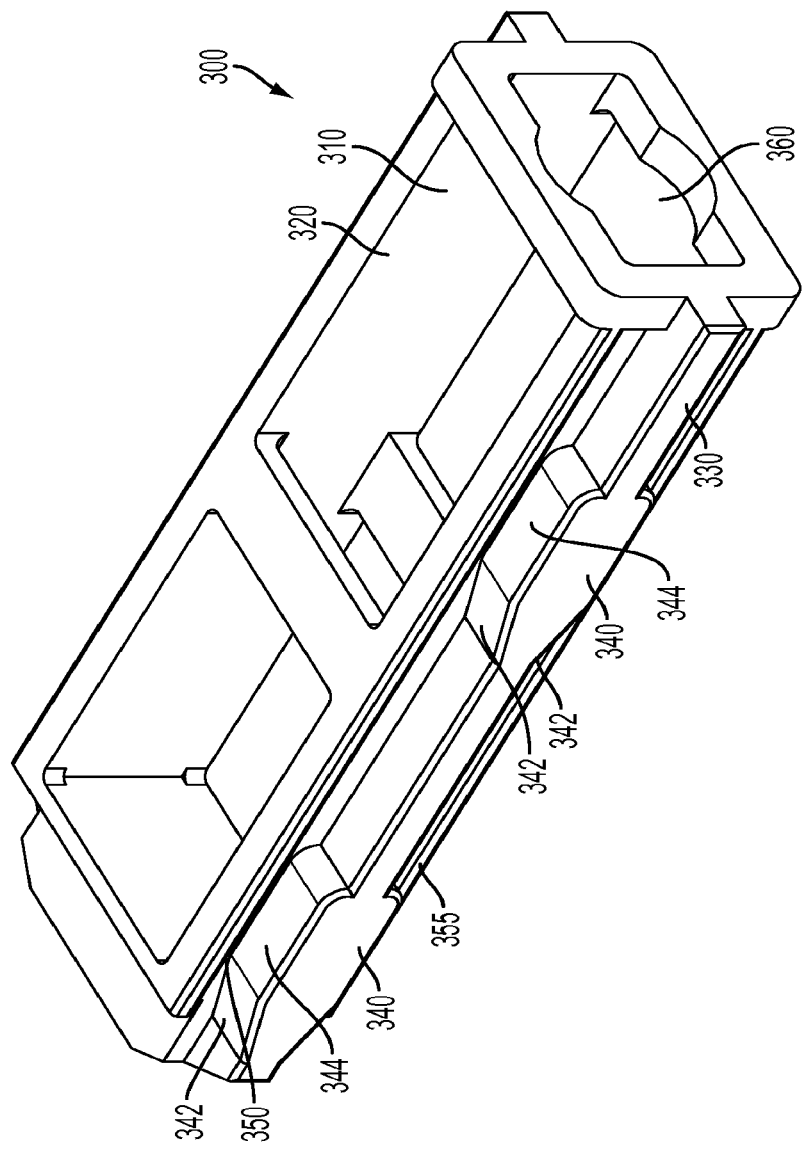
FIG. 4 is a perspective view of the insert of the expandable inter-body fusion device of FIG. 1.
Figure 5:
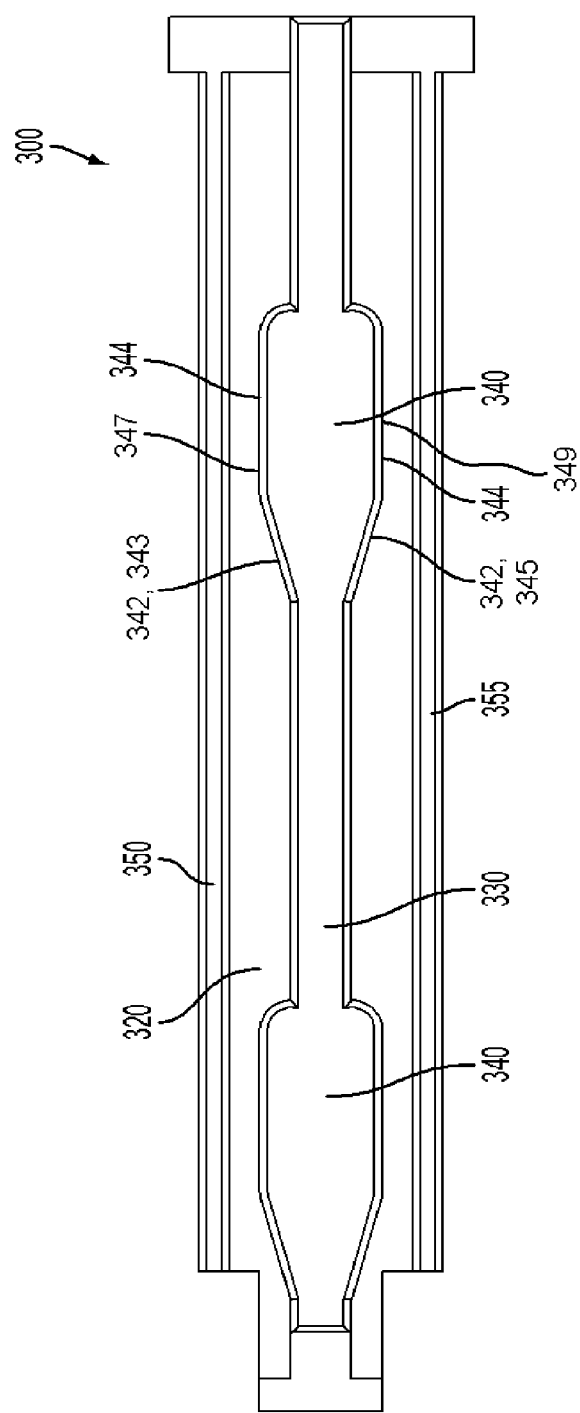
FIG. 5 is a side elevational view of the insert of FIG. 4.

Referring now to FIGS. 4 and 5, in one exemplified aspect, the insert 300 comprises a frame 310 with a plurality of longitudinal frame sides 320. In one aspect, a longitudinal rail 330 protrudes from the external surface of each of the longitudinal frame sides 320. In another aspect, each longitudinal rail comprises at least one ramp 340 having at least one inclined surface 342 and at least one substantially flat surface 344. As illustrated in FIG. 5, in a further aspect, each ramp can comprise an upper inclined surface 343, a lower inclined surface 345, an upper flat surface 347 and a lower flat surface 349. In this aspect the longitudinal rail 330 has a first rail thickness that corresponds to the distance between the upper flat surface and the lower flat surface of the ramp 340, and a second rail thickness in areas of the longitudinal rail that do not comprise the ramp. As can be appreciated, the second rail thickness can be less than the first rail thickness. In yet another aspect, each of the longitudinal rails 330 comprises a plurality of ramps. For example, each longitudinal rail can comprise a first ramp 340 spaced from a second ramp by a predetermined longitudinal distance along the longitudinal rail.

Correspondingly, in one aspect, each longitudinal sidewall 130 of the first plate 100 can substantially align with a longitudinal sidewall 230 of the second plate 200. For example, each longitudinal sidewall of the first plate can substantially overlie at least a portion of a longitudinal sidewall of the second plate. Each set of substantially aligned longitudinal sidewalls (a longitudinal sidewall 130 from the first plate 100 and a longitudinal sidewall 230 from the second plate 200) define at least one void 150, as illustrated in FIGS. 1 and 2. In another aspect, the at least one void can be sized and shaped to complimentarily accept a ramp 340 of the insert 300 therein. In this aspect, in a first unexpanded position (as illustrated in FIG. 2), each of the ramps of the insert can be positioned substantially within the void 150 formed between the substantially aligned longitudinal sidewalls 130, 230 of the first and second plates 100, 200. In the first unexpanded position, each longitudinal sidewall 130, 230 can be positioned substantially near or in contact with the respective longitudinal rail 330 of the insert 300. The first unexpanded position is the position in which the expandable inter-body fusion device 10 can be to be inserted between the adjacent vertebrae of a patient.

The expandable inter-body fusion device 10 can be selectively adjusted about and between the first unexpanded position, in which the ramps 340 of the insert 300 can be positioned substantially within the void 150 of the first and second plates 100, 200, and a second expanded position in which the ramps of the insert are not positioned substantially within the void. In one aspect, in the second expanded position, the flat surface 344 of the ramp can engage the inner surface 120 of the longitudinal sidewall 130 of the first plate 100 and/or the inner surface 220 of the longitudinal sidewall 230 of the second plate 200. As can be appreciated, in the second expanded position, the expandable inter-body fusion device 10 can have a height and interior cavity 15 volume that is greater than the height and interior cavity volume of the expandable inter-body fusion device in the first, unexpanded position. That is, in the first unexpanded position, the interior cavity 15 of the device can have a first cavity size, and in the second expanded position the interior cavity has a second cavity size that is greater than the first cavity size.

To expand the expandable inter-body fusion device 10 into the second expanded position, the insert 300 can be moved longitudinally from a first insert position, in which the ramps 340 of the insert 300 can be positioned substantially within the void 150 of the first and second plates 100, 200, toward either the trailing end 19 or the leading end 17 of the device to a second insert position, thereby moving the ramps 340 into contact with a portion of at least one of the longitudinal sidewalls 130, 230. In this position, the aligned longitudinal sidewalls of the first and second plates 100, 200 are separate by traveling up the inclined surfaces 342 of the ramp until the first plate and the second plate are separated and supported by the flat surfaces 344 of the ramp. In the second expanded position, portions of the longitudinal sidewalls are supported by the load bearing properties of the flat surfaces of the ramps. As one skilled in the art can appreciate, the amount of separation achievable between the first plate and the second plate can be determined by the height of the ramp.

As shown in the figures, the ramps 340 can be double inclined, with two inclined surfaces 342 (upper inclined surface 343 and lower inclined surface 345) and two flat surfaces 344 (upper flat surface 347 and lower flat surface 349). In this aspect, each inclined surface can be configured to cam the longitudinal sidewall 130, 230 of one of the first plate 100 or the second plate 200 and each flat surface 344 configured to support a portion of the respective longitudinal sidewall. However, it is contemplated that the ramps can be single inclined, with only one inclined surface and one flat per ramp. In this aspect, the opposing surface would remain substantially adjacent and parallel to the respective longitudinal sidewall.

Figure 26:
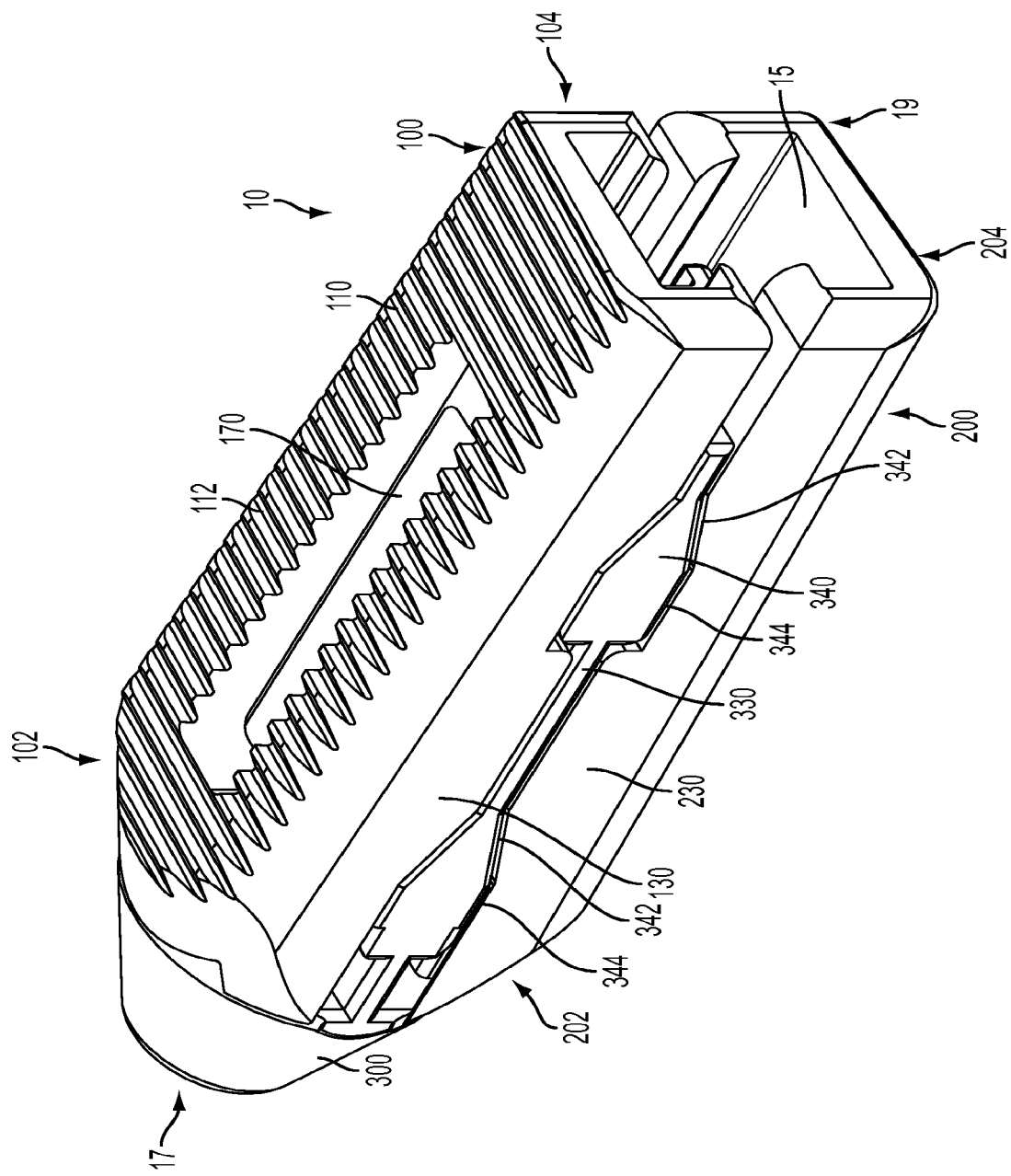
FIG. 26 is a perspective view of one aspect of an expandable inter-body fusion device that is expanded by moving an insert toward the trailing end of the device, in the first unexpanded position.

In one aspect, the inclined surface 342 leads the ramp 340, as shown in FIGS. 1 and 2. That is, the inclined surface of each ramp is positioned between the leading end 17 of the expandable inter-body fusion device 10 and the flat surface 344 of each ramp 340. As such, moving the insert 300 longitudinally toward the leading end 17 of the device moves the device 10 from the first unexpanded position, to the second expanded position. Optionally, however, in another aspect, the inclined surface can trail the ramp, as shown in FIG. 26. That is, in this aspect, the inclined surface 342 of each ramp 340 can be positioned between the trailing end 19 of the expandable inter-body fusion device and the flat surface 344 of each ramp. Accordingly then, moving the insert 300 longitudinally toward the trailing end 19 of the expandable inter-body fusion device 10 can move the device into the second expanded position.

With reference to FIG. 5, in an exemplified aspect, the insert 300 can have a first longitudinal tongue 350 extending from the external surface of each of the longitudinal frame sides 320 and a second longitudinal tongue 355 extending from the external surface of each of the longitudinal frame sides 320. In another aspect, the first longitudinal tongue can be spaced from the second longitudinal tongue a predetermined distance. In yet another aspect, the first longitudinal tongue 350 can be positioned near or adjacent to an upper edge of the longitudinal frame sides, and the second longitudinal tongue 355 can be positioned near or adjacent to a lower edge of the longitudinal frame sides 320. In a further aspect, the first longitudinal tongue can be substantially parallel to the second longitudinal tongue. Optionally, however, the first the first longitudinal tongue 350 can be at an angle relative to the second longitudinal tongue 355.

Correspondingly, in one aspect, the first plate 100 can define a groove, recess, or lip 160 in each longitudinal sidewall (as illustrated in FIG. 6) that is configured to mate with the first longitudinal tongue 350 of the insert 300. In another aspect, the second plate 200 can define a groove, recess, or lip 260 configured to mate with the second longitudinal tongue 355 of the insert. The first longitudinal tongue and the second longitudinal tongue can be configured to move within the groove or recess to allow expansion of the device. In another aspect, at least one of the groove, recess, and lip 160, 260 of the first and second plates 1000, 200 can engage the first longitudinal tongue 350 or the second longitudinal tongue 355 to retain the first and second plates to the insert 300 after expansion. Of course, it is contemplated that the groove and tongue relationship can be reversed.

Figure 23:
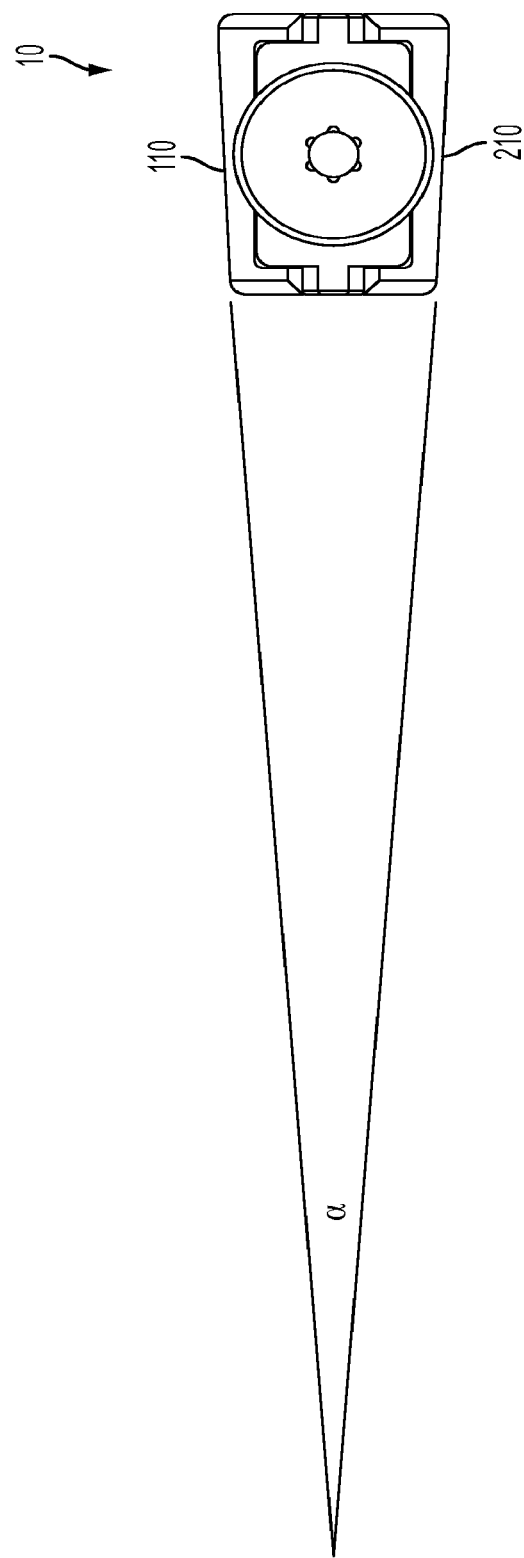
FIG. 23 is a trailing end elevational view of the expandable inter-body fusion device FIG. 19, illustrating the transverse angle.
Figure 24:
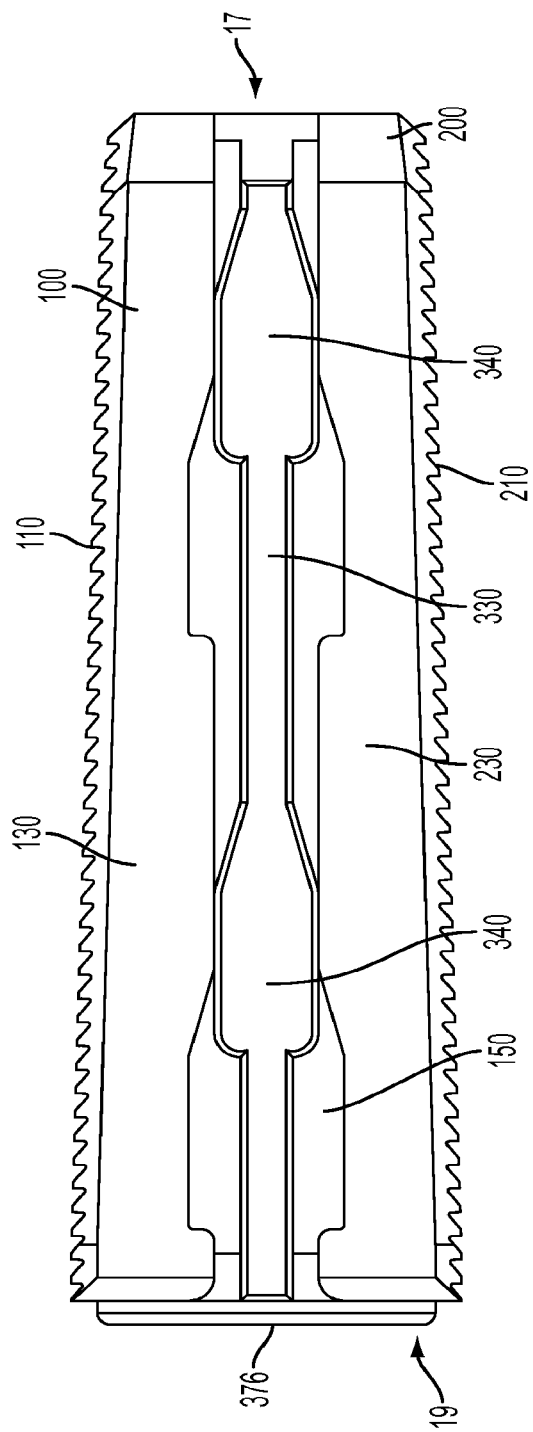
FIG. 24 is a side elevational view of the expandable inter-body fusion device of FIG. 19 in the second expanded position.
Figure 25A:
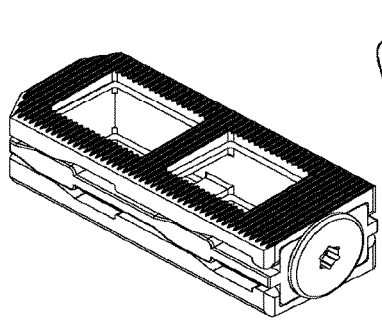
FIGS. 25A-25I are a series of perspective views of an expandable inter-body fusion device used in an anterior OLIF approach.
Figure 25B:
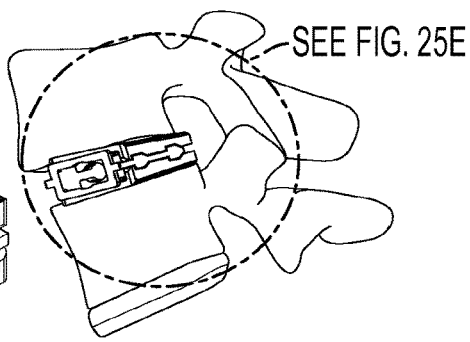
Figure 25C:
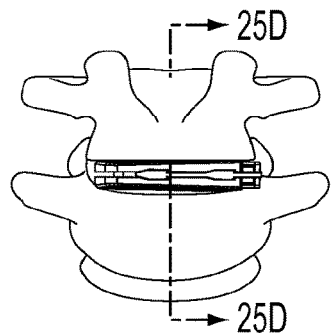
Figure 25D:
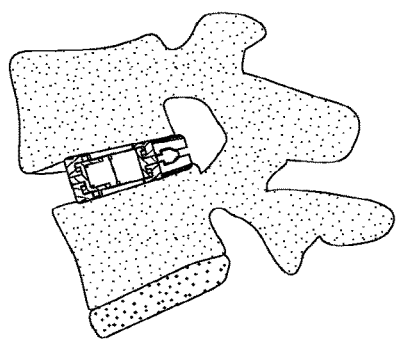
Figure 25E:
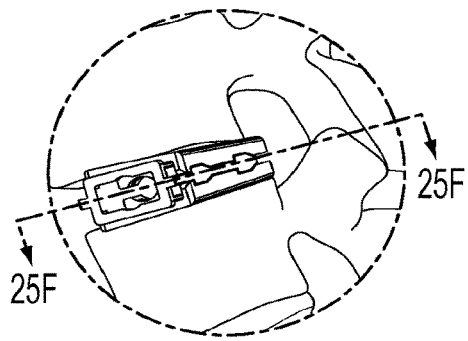
Figure 25F:
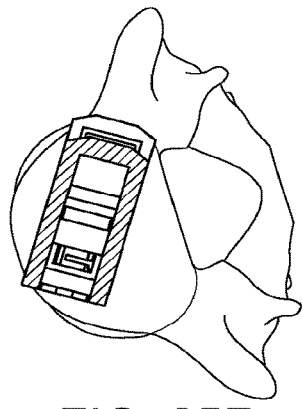
Figure 25G:
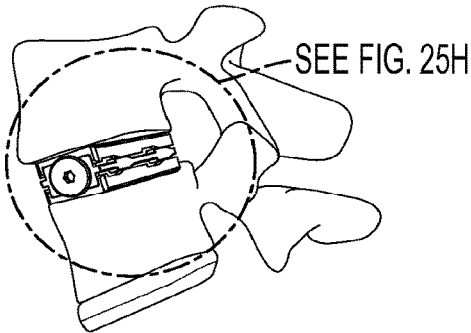
Figure 25H:
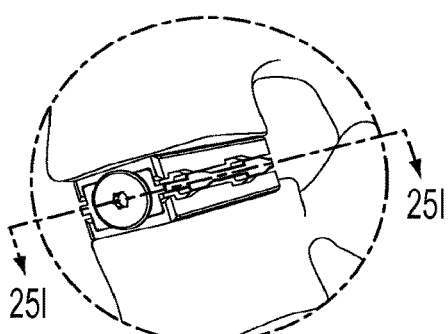
Figure 25I:
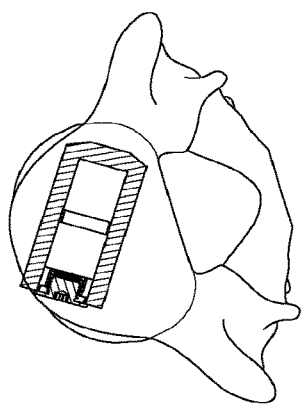

It is contemplated that this technology can be used for a variety of implants used for a variety of spinal procedures. As mentioned before, these procedures include, but are not limited to OLIF, DLIF, PLIF, ALIF, TLIF, and LLIF. Because of this, depending upon the procedure and point of insertion for the implant, the geometry of the implant can differ. For example, in a DLIF expandable device, the approach is lateral. As such, the upper bone contact surface 110 can be transversely angled with respect to the lower bone contact surface 210 from a first sidewall to a second sidewall to match, increase, or decrease lordosis, as shown in FIGS. 3 and 23. Note, however, that the expandable inter-body fusion device 10 is not necessarily angled longitudinally from the leading end 17 of the device to the trailing end 19 of the 10. The degree of transverse angle α can vary from about 0 degrees to about 15 degrees. In another aspect, the transverse angle α can vary from about 4 degrees to about 12 degrees. In yet another aspect, the transverse angle α can vary from about 6 degrees to about 8 degrees. The expandable inter-body fusion device 10 can expand in height a distance from about 1 mm to about 5 mm, depending on the original height of the device, the size of the void 150 of the first and second plates 100, 200 and/or the height of the ramps 340 of the insert 300. In this example, the insert 300 can expand the device symmetrically.

Figure 21:
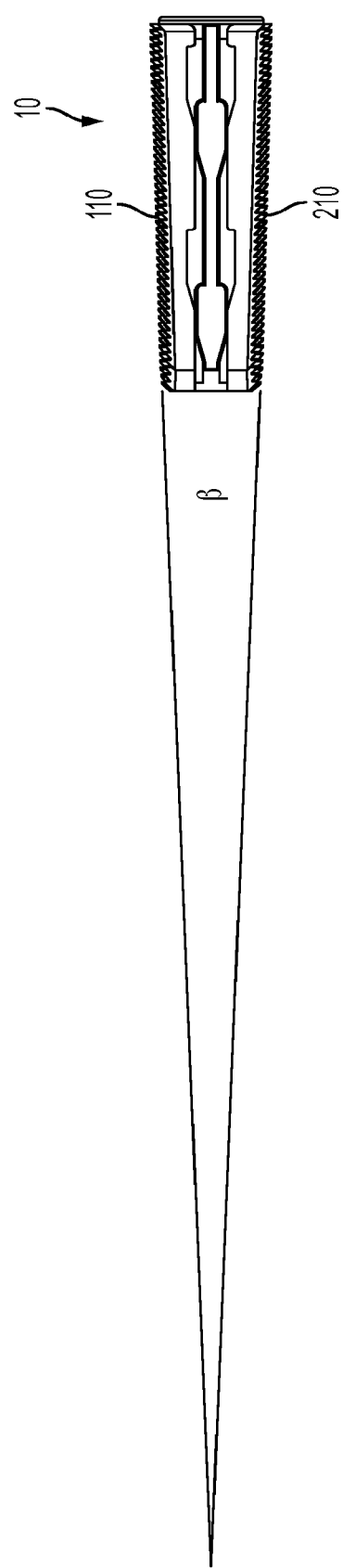
FIG. 21 is a side elevational view of the expandable inter-body fusion device of FIG. 19, illustrating the longitudinal angle.
Figure 22:
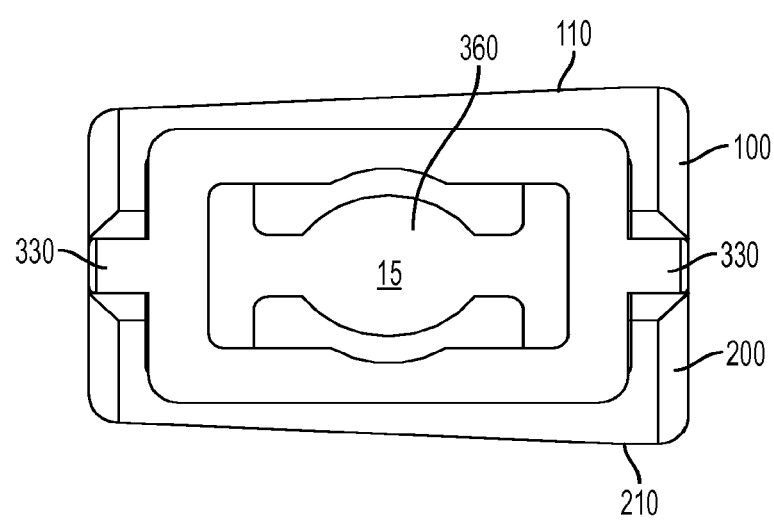
FIG. 22 is a side elevational view of the expandable inter-body fusion device FIG. 19, illustrating an aspect that is angled transversely.

In an OLIF procedure, the expandable inter-body fusion device 10 can be inserted obliquely, either anteriorly or posteriorly. As such, similar to the DLIF implant, the upper bone contact surface 110 can be angled transversely with respect to the lower bone contact surface 210 from the first sidewall to the second sidewall depending on the need to match, increase, or decrease lordosis. In addition, the upper bone contact surface can also be angled longitudinally with respect to the lower bone contact surface from the leading end 17 of the device to the trailing end 19, as illustrated in FIG. 21. In one aspect, a longitudinal angle β between the upper bone contact surface 110 and the lower bone contact surface can vary from about 0 degrees to about 15 degrees. In another aspect, the longitudinal angle β can vary from about 4 degrees to about 12 degrees. In yet another aspect, the longitudinal angle β can vary from about 6 degrees to about 8 degrees. The combination of longitudinal angle β and transverse angle α can vary depending about the angle of insertion. It would be desired to at least substantially fit the expandable inter-body fusion device 10 with the particular insertion approach angle so that the resulting combined angle is substantially posterior-anterior only or not at all. Thus, while the upper bone contact surface 110 can be angled with respect to the lower bone contact surface 210 in two planes, the device substantially ensures orthogonal lordosis.

In an exemplified aspect, at least one of the first plate 100 and the second plate 200 can define at least one graft window 170, 270 that is in communication with the interior cavity 15. The at least one graft window 170 defined in the first plate can overlie at least a portion of the at least one graft window 270 of the second plate, thereby permitting bone growth therethrough. In another aspect, the upper bone contact surface 110 of the first plate 100 comprises ridges 112 for frictionally engaging a first vertebra of the patient. As can be appreciated, the lower bone contact surface 210 of the second plate can comprise ridges 212 to frictionally engage a second vertebra of the patient.

In one aspect, the leading end 17 of the expandable inter-body fusion device 10 can be tapered to facilitate insertion. For example, a leading portion of the first plate 100, the second plate 200, and/or the insert 300 can be tapered to facilitate insertion. In another aspect and as illustrated in FIGS. 3 and 4, the trailing end 19 of the insert can define an aperture 360 in communication with the interior cavity 15. The aperture 360 can facilitate the passage of bone growth material, such as for example and not meant to be limiting, autograft or allograft bone product, or synthetic bone substitute, and the like. In this fashion, the interior cavity 15 can be packed with bone growth material after the expandable inter-body fusion device 10 has been expanded to the second expanded position.

Figure 27:
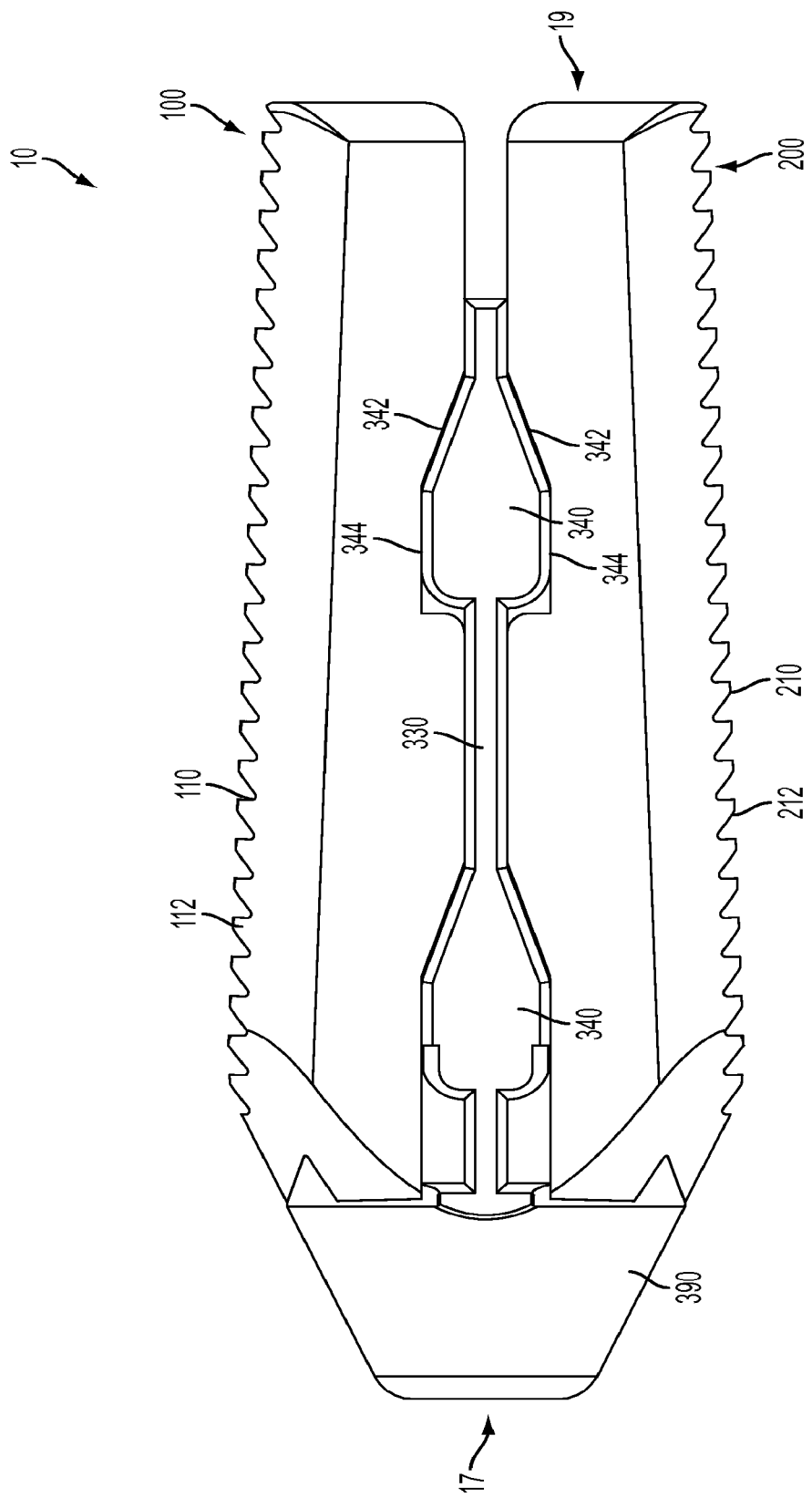
FIG. 27 is a side elevational view of the expandable inter-body fusion device of FIG. 26.

In one aspect, the device can also comprise an endcap 370 configured to engage the insert, as illustrated in FIG. 7. For example, where the expandable inter-body fusion device 10 is expanded to the second expanded position by pulling the insert 300 from the leading end 17 toward the trailing end 19, the endcap can be used to maintain the device in the second expanded position. In another aspect, the endcap can be sized and shaped so that a portion of the endcap 370, such as a flange and the like, can extend past the peripheral edge of the aperture 360 of the insert 300. In this aspect, when the endcap is engaged with the insert, the endcap 370 can prevent the insert 300 from moving back toward the leading end of the device. As one skilled in the art can appreciate, movement of the insert back toward the leading end 17 could result in the undesired movement of the inter-body fusion device from the second expanded position toward the first unexpanded position. In a further aspect, portions of the trailing end of the device, such as portions of the first plate 100, the second plate 200 and/or the insert 300 can be threaded to facilitate the complimentary threading of the endcap. Additionally, the threaded trailing end of the device 10 can also be used to engage the distal end of the insertion tool (not shown) and permit the movement of the insert with respect to the first and second plates. In yet another aspect, a leading end of the insert can comprise a tapered nose 390, as shown in FIG. 27.

Figure 11:
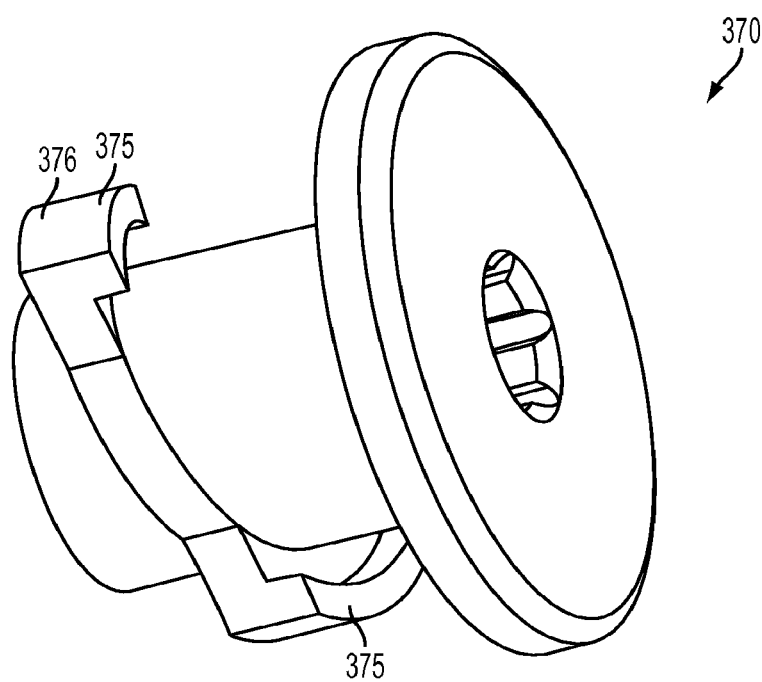
FIG. 11 is perspective view of an endcap having a single lead cam lock.
Figure 12:
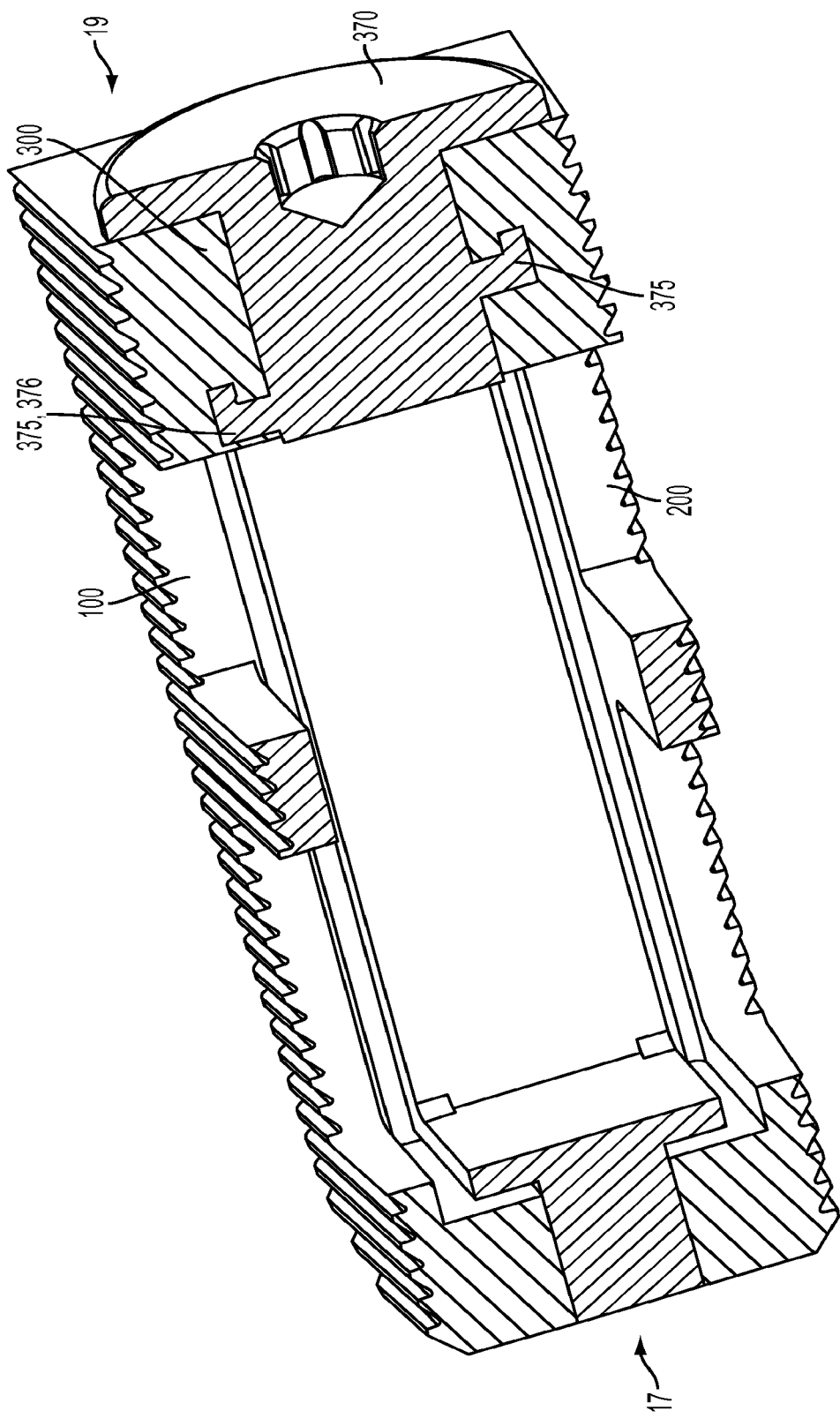
FIG. 12 is a cutaway perspective view of an expandable inter-body fusion device in the second expanded position and having the endcap of FIG. 11.
Figure 13:
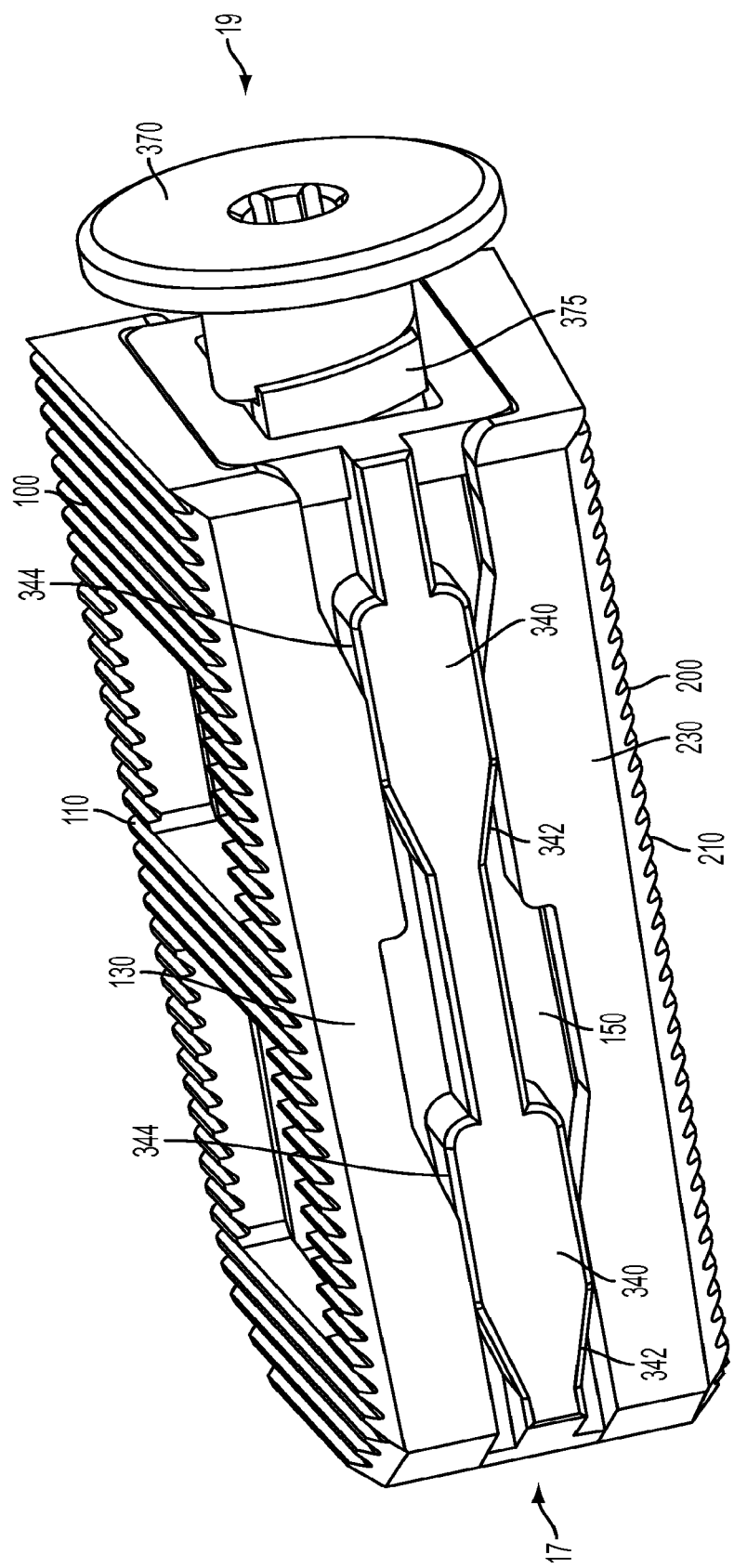
FIG. 13 is a perspective view of the expandable inter-body fusion device of FIG. 12.
Figure 14:
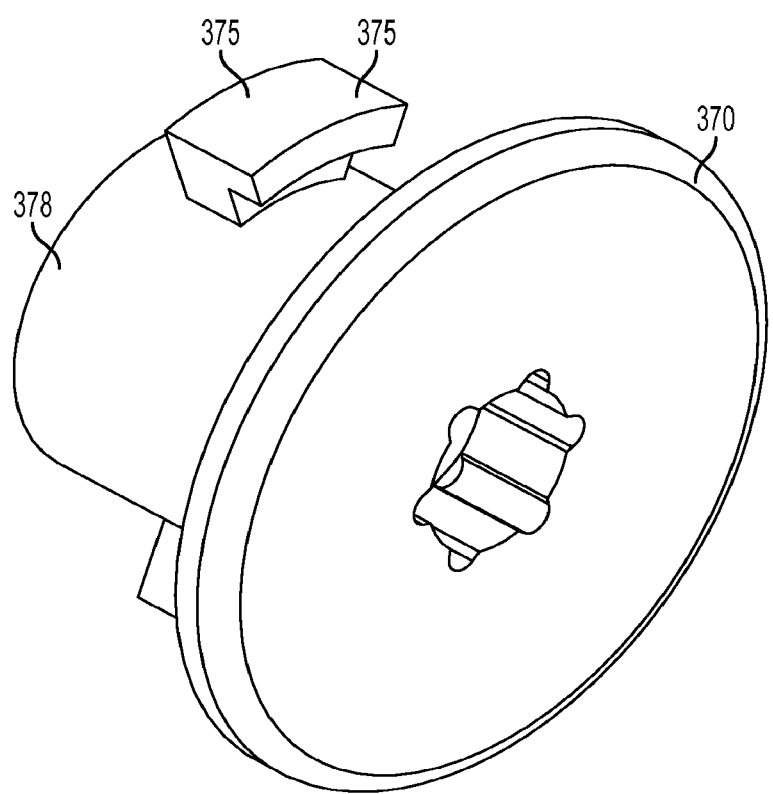
FIG. 14 is a perspective view of an endcap coupled to a boss.

In another aspect, where the expandable inter-body fusion device 10 is expanded to the second expanded position by pushing the insert 300 from the trailing end 19 toward the leading end 17, the device can further comprise a structure to facilitate securing the insert to a portion of the first plate 100 and/or the second plate 200, or to an adjacent vertebra of the patient. For example, in one aspect and as illustrated in FIG. 11, the endcap 370 comprises a lock 376 configured to matingly engage a portion of the first and second plates 100, 200. In one aspect, the lock comprises at least one lead 375. In another aspect, the lock can be a single or dual lead cam lock. The leads can be tapered or square ended. In this aspect, the endcap can be inserted through the aperture 360 defined in the trailing end 19 of the device and into the interior cavity 15 with the leads rotated to a first orientation in which the leads 375 do not engage the device (as illustrated in FIG. 13). Upon entering the cavity, the endcap can be rotated to a second orientation in which the leads engage a portion of at least one of the first and second plates 100, 200.

Figure 15:
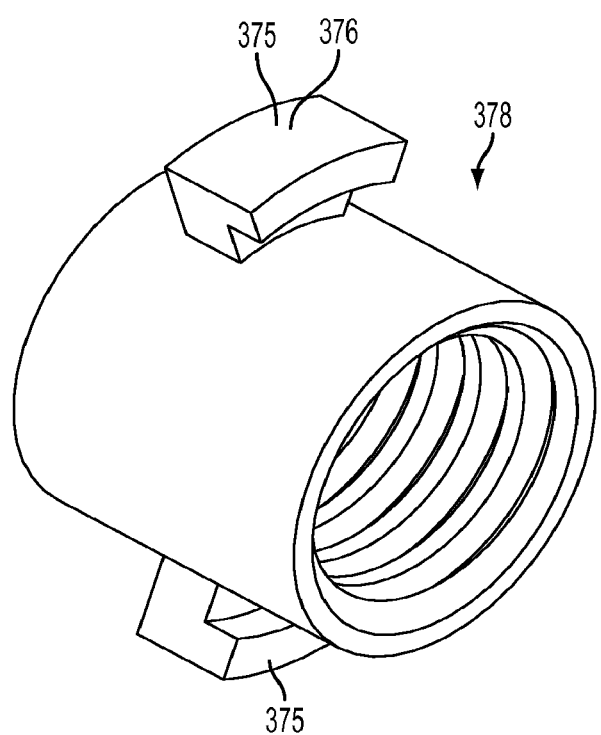
FIG. 15 is a perspective view of the boss of FIG. 14.
Figure 16:
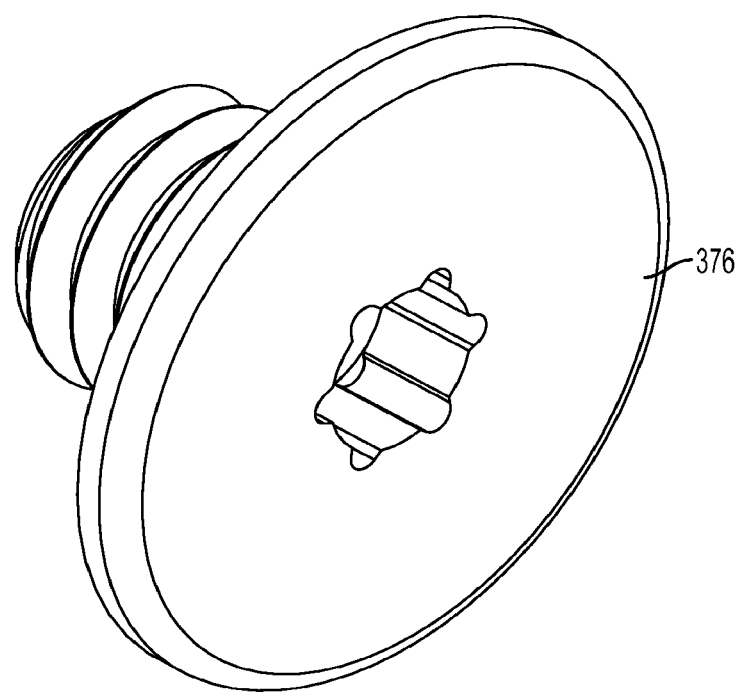
FIG. 16 is a perspective view of the endcap of FIG. 14.
Figure 17:
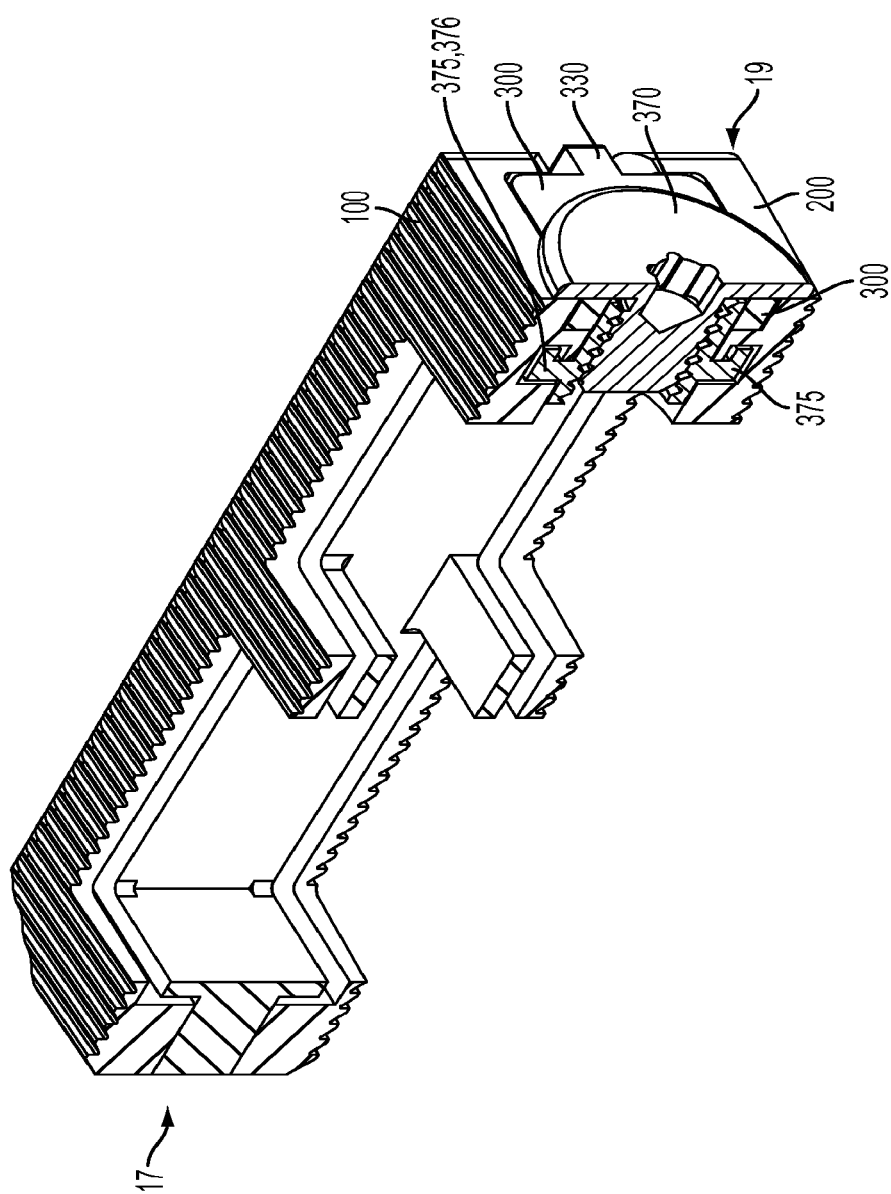
FIG. 17 is a cutaway perspective view of an expandable inter-body fusion device in the second expanded position having an endcap and boss as in FIG. 14.
Figure 18A:
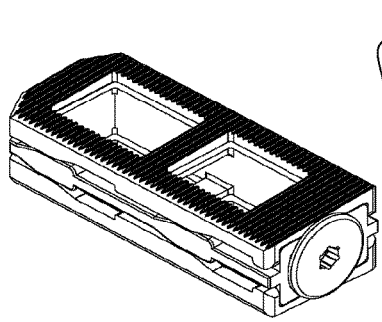
FIGS. 18A-18I are a series of perspective views of an expandable inter-body fusion device used in a DLIF approach.
Figure 18B:
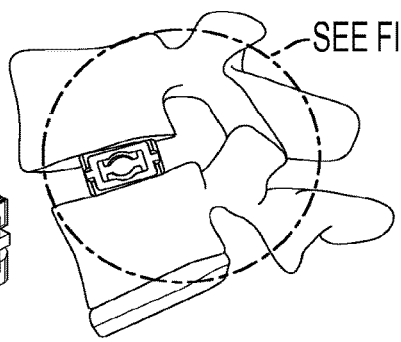
Figure 18C:
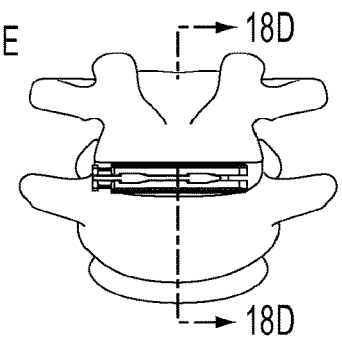
Figure 18D:
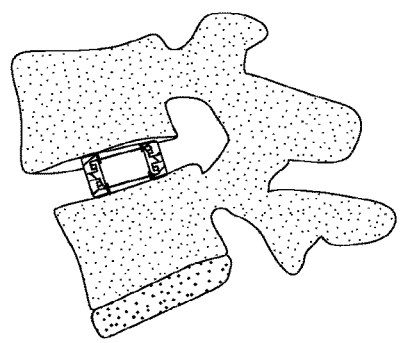
Figure 18E:
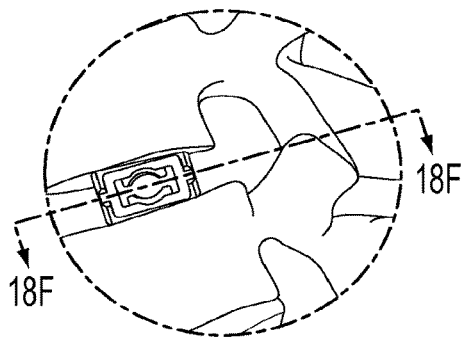
Figure 18F:
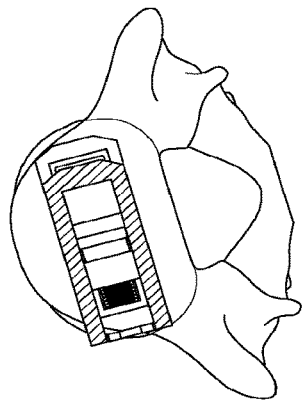
Figure 18G:
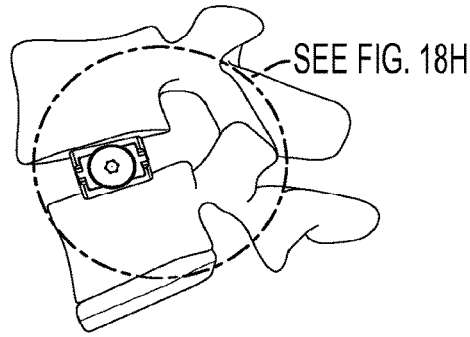
Figure 18H:
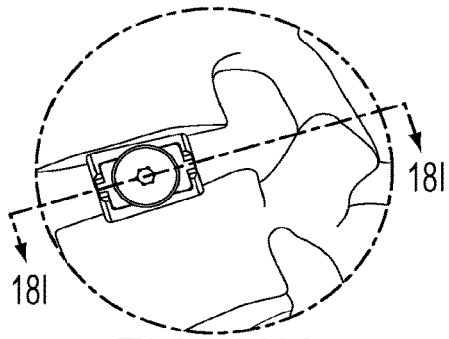
Figure 18I:
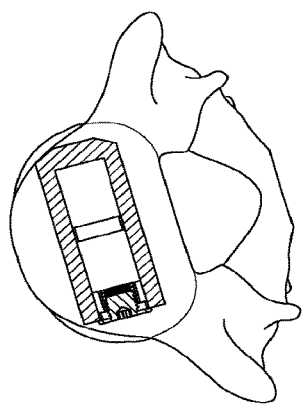
Figure 19:
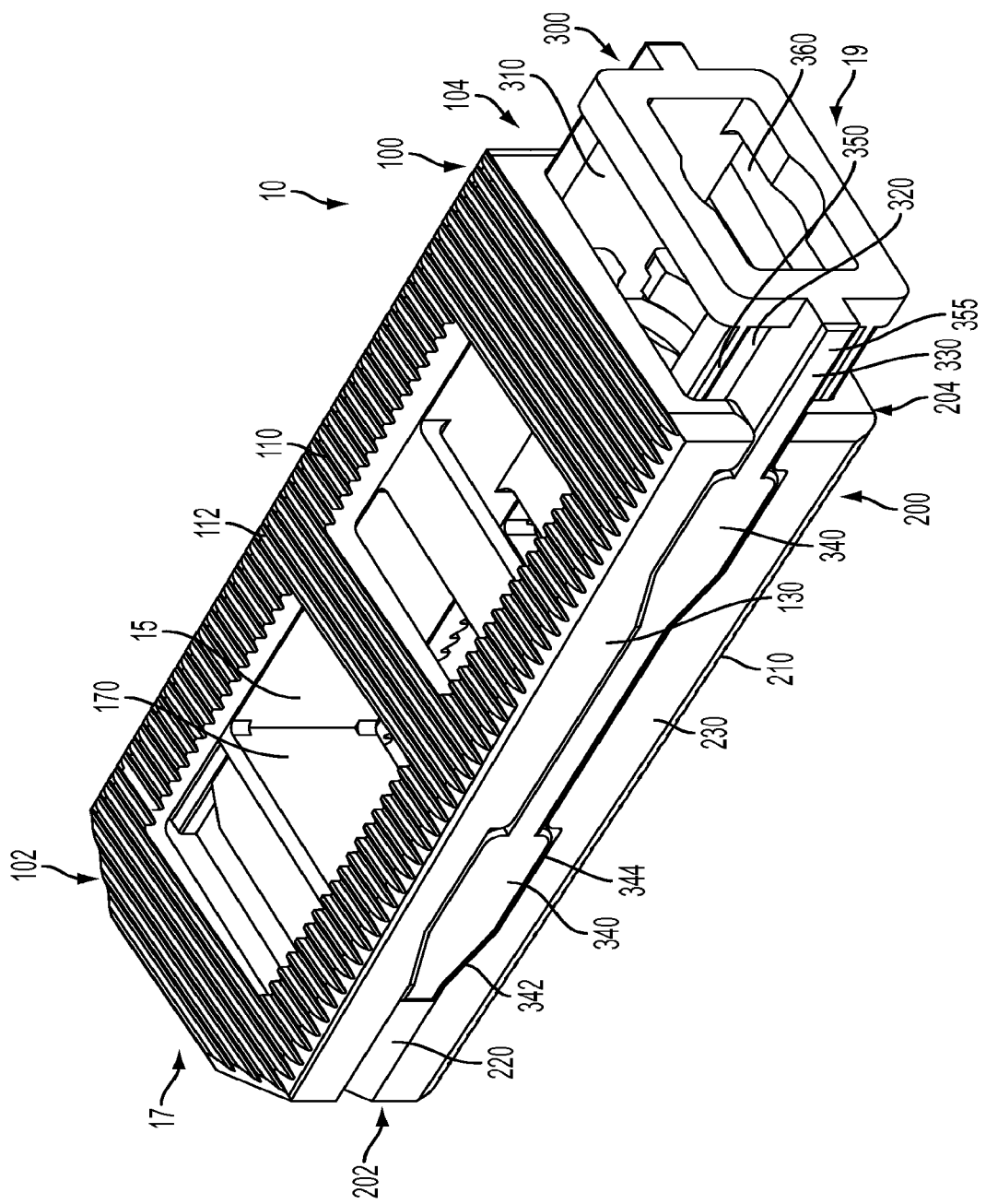
FIG. 19 is a perspective view of one aspect of an expandable inter-body fusion device that is expanded by moving an insert toward the leading end of the device, in the first unexpanded position.
Figure 20:
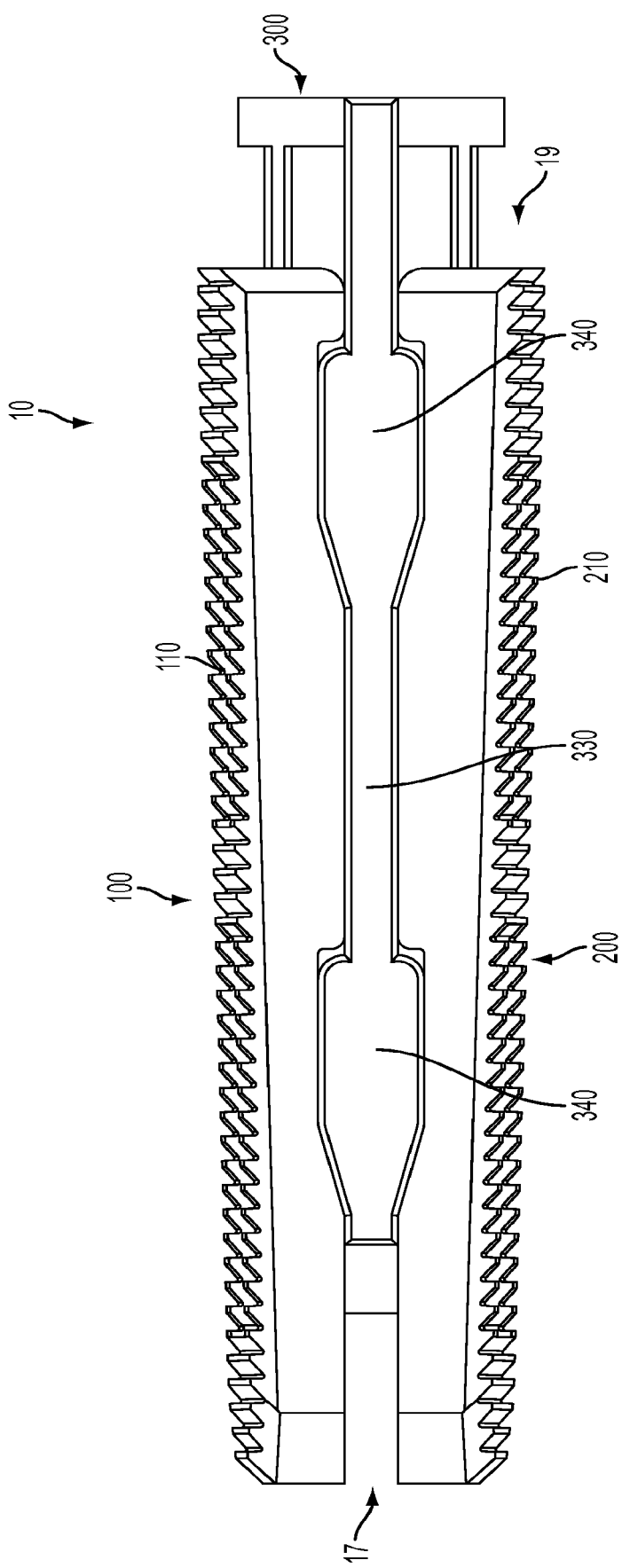
FIG. 20 is a side elevational view of the expandable inter-body fusion device of FIG. 19, illustrating an aspect that is angled longitudinally, in the first unexpanded position.

In another aspect and as illustrated in FIGS. 15-17, the endcap can further comprise a boss 378 having a lock 376. In one aspect, the lock comprises at least one lead 375. In another aspect, the lock can be a single or dual lead cam lock. In this aspect, the boss can define internal threads that are complimentarily sized to engage external threads positioned on a portion of the endcap 370. In use, then, the lock 376 of the boss can be configured to engage a portion of the first and second plates 100, 200, and the end cap can engage the boss. In still another aspect, either the endcap itself or a separate boss can comprise radially extending blades (not shown) that, when rotated, are configured to engage the adjacent bony structure to retain the expandable inter-body device in the desired position. It is also contemplated that the inner surface 120, 220 of the first and second plates can have a threaded portion to engage an endcap 370 having external threads.

Figure 28:
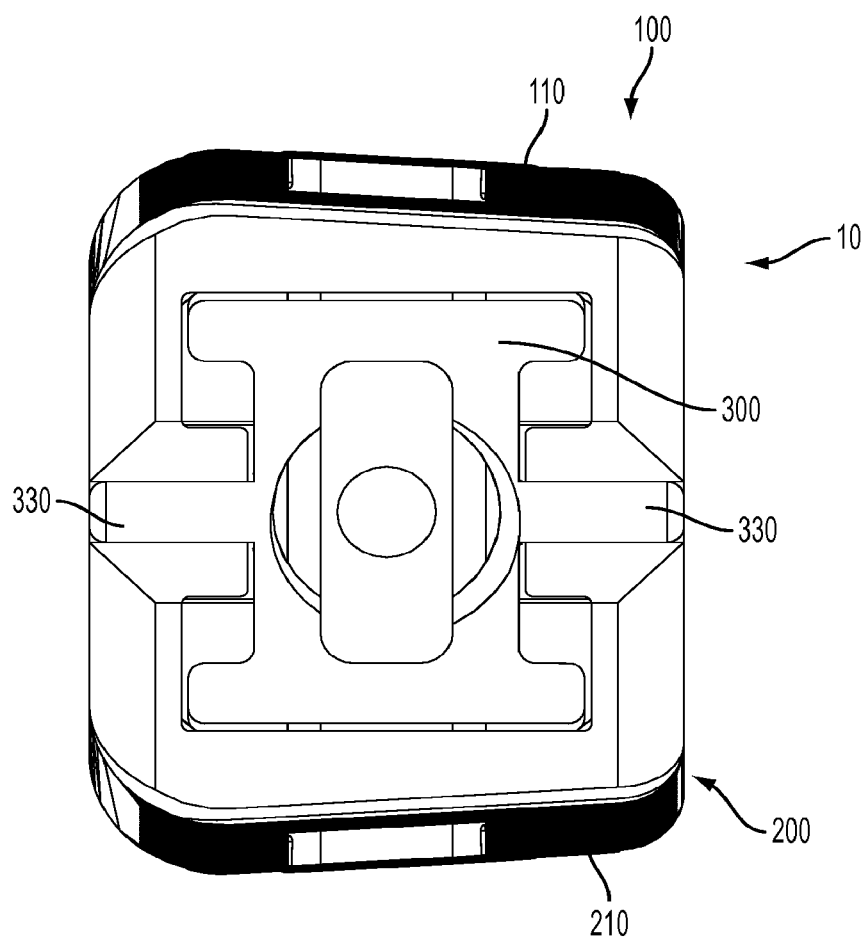
FIG. 28 is a trailing end elevational view of the expandable inter-body fusion device FIG. 26.
Figure 29:
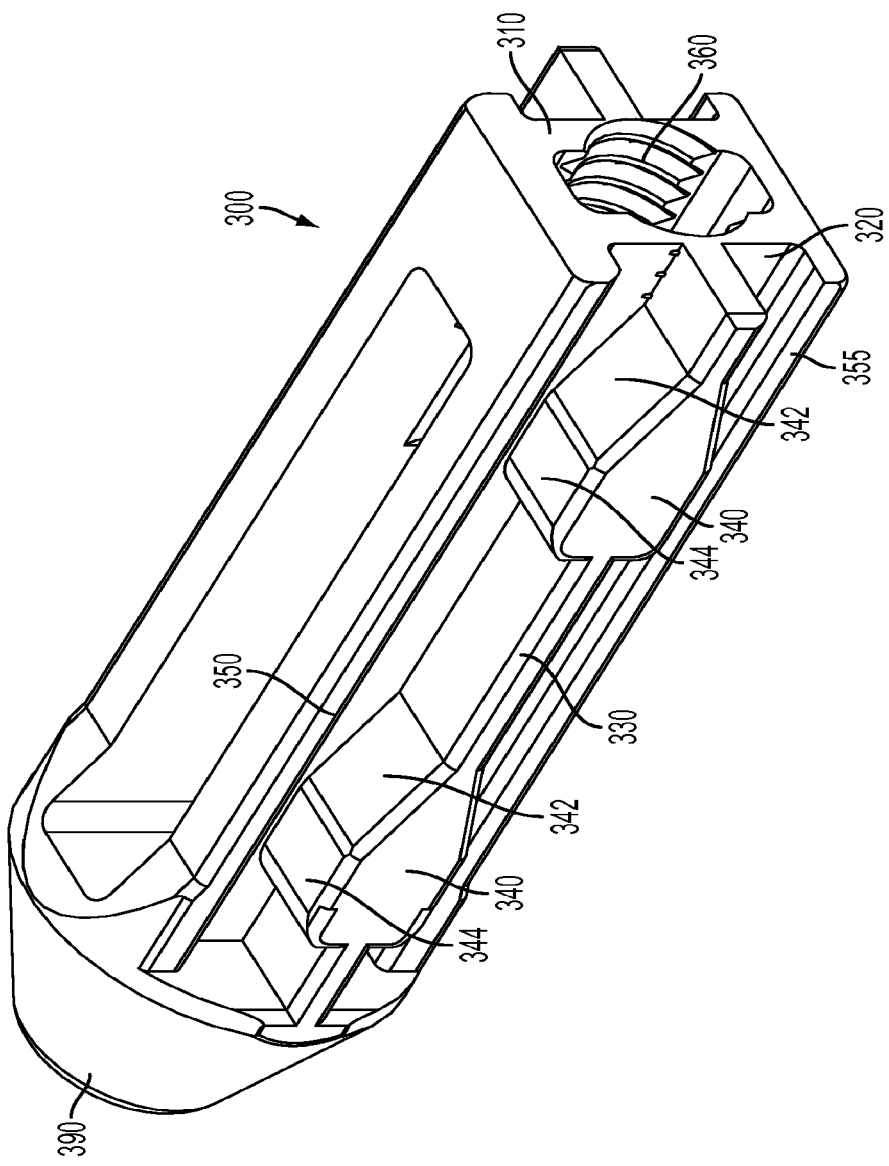
FIG. 29 is a perspective view of the insert of the expandable inter-body fusion device of FIG. 26.
Figure 31A:
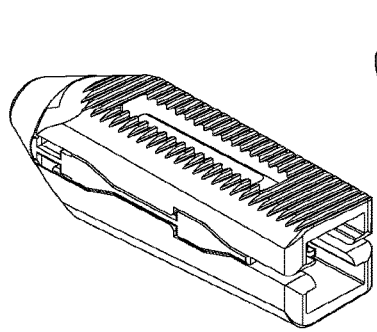
FIGS. 31A-31I are a series of perspective views of an expandable inter-body fusion device used in a posterior OLIF approach.
Figure 31B:
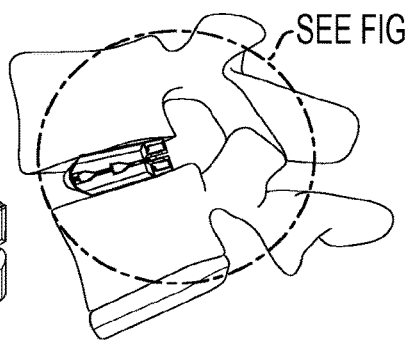
Figure 31C:
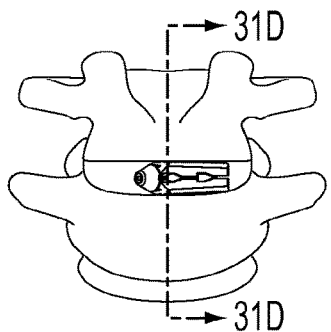
Figure 31D:
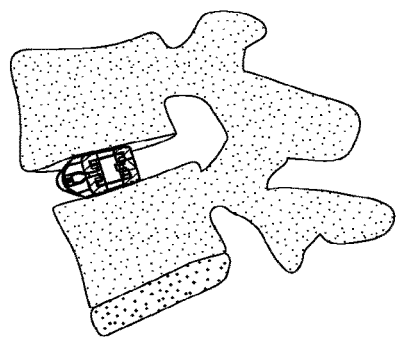
Figure 31E:
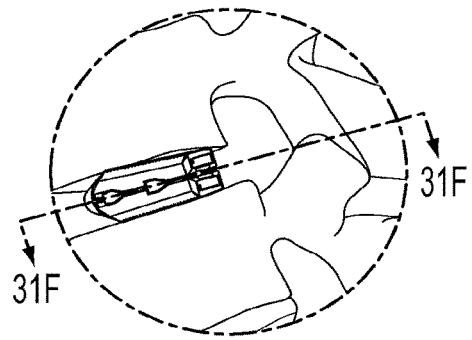
Figure 31F:
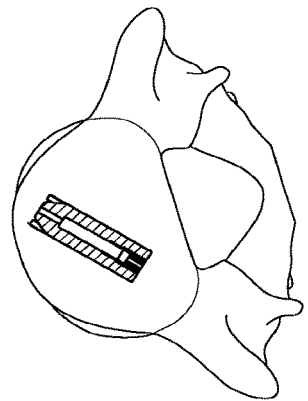
Figure 31G:
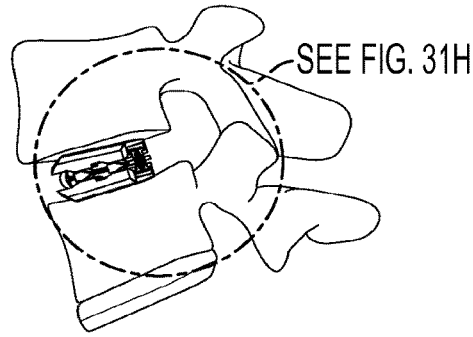
Figure 31H:
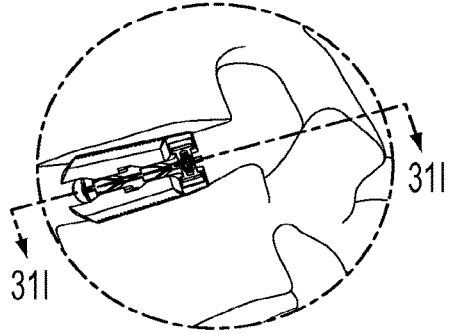
Figure 31I:
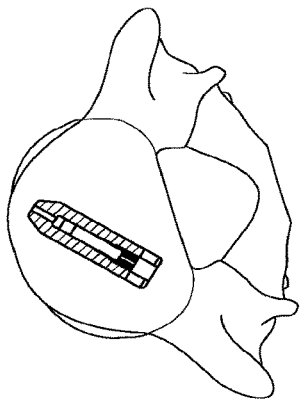

In one aspect, as shown in FIG. 28, the expandable inter-body fusion device 10 can be longitudinally cannulated. This aspect enables the device to be inserted over a guide wire. As one skilled in the art can appreciate, in an exemplified aspect, the insertion tool would necessarily have to be cannulated.

Also presented herein is a method of using an expandable inter-body fusion device 10 during an inter-body fusion procedure. In one aspect, the method comprises accessing the desired disc space, choosing the correct expandable inter-body fusion device size with the appropriate height and angle, inserting the expandable inter-body fusion device 10 into the desired area in the disc space, expanding the expandable inter-body fusion device from the first unexpanded position to the second expanded position with longitudinal movement of the insert 300, and securing the insert to the first and second plates 100, 200. An additional step of packing the interior cavity 15 via the aperture 360 in the trailing end 19 of the expandable inter-body fusion device with bone fusion material either prior to or after expansion is also contemplated. In one aspect, the step of securing the insert to the first and second plates can be replaced by securing the expandable inter-body fusion device 10 to the surrounding bony structure. In another aspect, the step of expanding the inter-body fusion device comprises the step of moving the insert 300 with respect to the first and second plates 100, 200 toward the trailing end 19 of the expandable inter-body fusion device. In still another aspect, the step of expanding the expandable inter-body fusion device 10 comprises the step of moving the insert with respect to the first and second plates toward the leading end 17 of the expandable inter-body fusion device.

In one aspect, the step of choosing the correct expandable inter-body fusion device 10 size with the appropriate height and angle comprises placing an undersized trial device in the disc space, expanding the trial device to the second expanded position, and repeating until the correct height and lordosis is found. The trial height and angle gives the information to prescribe the correct expandable inter-body fusion device for the procedure.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An expandable inter-body fusion device for use in surgery comprising:
   a first plate having an upper bone contact surface, an opposed first inner surface and at least one longitudinal sidewall;
   a second plate underlying at least a portion of the first plate, the second plate having a lower bone contact surface, an opposed second inner surface and at least one longitudinal sidewall; and
   an insert comprising a frame having opposed longitudinally extending lateral sides from each of which a respective longitudinal rail protrudes laterally, each longitudinal rail extending continuously and comprising a plurality of ramps including a pair of the plurality of ramps being longitudinally spaced on each opposed lateral extending side, each ramp of the plurality of ramps having at least one inclined surface and at least one substantially flat surface that define contours of the respective rail in a vertical direction,
   wherein the insert is positionable in abutting relationship between the first and second plates with the longitudinal sidewalls substantially aligned to form a set of aligned sidewalls defining a plurality of voids therebetween, wherein the expandable inter-body fusion device is selectively adjustable between
   an unexpanded position, in which the insert is in abutting relationship with the first and second plates and the device has an interior cavity having a first cavity size, and in which each of the plurality of ramps of the insert is positioned substantially within a respective void of the plurality of voids, and
   an expanded position, in which the insert is in abutting relationship with the first and second plates and the interior cavity has a second cavity size greater than the first cavity size, and in a fully expanded position the at least one substantially flat surface of each of the ramps of the plurality of ramps of the insert abuts at least a flat portion of the sidewalls of the first and second plates to maintain the expandable inter-body fusion device in the fully expanded position supported at four spaced locations by the abutting flat surfaces of the ramps and respective sidewalls, and
   wherein the device is transitioned from the unexpanded position to the expanded position by longitudinally sliding the insert with respect to the first and second plates, thereby causing the at least one inclined surface of each of the ramps to exit its respective void and engage a portion of the sidewalls of the first and second plates to drive them apart.

2. The device of claim 1, wherein the plurality of voids has each void of the plurality of voids sized and shaped to complimentarily accept a ramp of the plurality of ramps of the insert therein.

3. The device of claim 1, wherein the first plate is at a transverse angle relative to the second plate.

4. The device of claim 1, wherein the at least one inclined surface comprises an upper inclined surface and a lower inclined surface, and the at least one substantially flat surface comprises an upper flat surface and a lower flat surface.

5. The device of claim 1, wherein the insert is movable about and between a first insert position, in which the device is in the unexpanded position, and a second insert position, in which the device is in the expanded position.

6. The device of claim 5, wherein in the second insert position, the at least one substantially flat surface supports at least a portion of the longitudinal sidewall of at least one of the first and second plates.

7. The device of claim 5, wherein upon movement about and between the first insert position and the second insert position, the at least one inclined surface cams a portion of the longitudinal sidewall of at least one of the first and second plates.

8. The device of claim 5, wherein the device has a leading end and a trailing end.

9. The device of claim 8, wherein the at least one inclined surface of the plurality of ramps is positioned between the leading end of the device and the at least one substantially flat surface of the plurality of ramps.

10. The device of claim 8, wherein the at least one inclined surface of the plurality of ramps is positioned between the trailing end of the device and the at least one flat surface of the plurality of ramps.

11. The device of claim 1, further comprising an endcap configured to engage a portion of at least one of the first plate, the second plate and the insert to maintain the insert in a desired position.

12. The device of claim 11, wherein portions of a trailing end of the device are threaded to matingly engage complimentary threading on the endcap.

13. The device of claim 12, wherein an aperture in communication with the interior cavity is defined in a trailing end of the device.

14. The device of claim 13, wherein the endcap is rotatable about and between a first orientation, in which the complimentary thread of the end cap can be inserted through the aperture and into the interior cavity, and a second orientation, in which at least a portion of the complimentary thread of the end cap engages the thread of at least one of the first and second plates of the trailing end of the device.

15. The device of claim 11, wherein the endcap comprises a cam lock having at least one lead configured to matingly engage a portion of at least one of the first and second plates.

16. An expandable inter-body fusion device for use in surgery comprising:
 a first plate having an upper bone contact surface, an opposed first inner surface and at least one longitudinal sidewall;
 a second plate underlying at least a portion of the first plate, the second plate having a lower bone contact surface, an opposed second inner surface and at least one longitudinal sidewall; and
 an insert comprising a frame having opposed longitudinally extending lateral sides from each of which a respective longitudinal rail protrudes laterally and extends longitudinally continuously, each longitudinal rail comprising a plurality of ramps including a pair of the plurality of ramps being longitudinally spaced on each opposed lateral extending side, each ramp of the plurality of ramps having at least one inclined surface and at least one substantially flat surface that define contours in a vertical direction of the respective rail,
 wherein the insert is positionable in abutting relationship between the first and second plates with the longitudinal sidewalls substantially aligned to form a set of aligned sidewalls defining a plurality of voids therebetween, wherein the expandable inter-body fusion device is selectively adjustable between an unexpanded position, in which the device has an interior cavity having a first cavity size and each of the plurality of ramps of the insert is positioned substantially within a respective void of the plurality of voids, and an expanded position, in which the interior cavity has a second cavity size greater than the first cavity size, and in a fully expanded position the at least one substantially flat surface of each of the ramps of the plurality of ramps of the insert abuts at least a flat portion of the sidewalls of the first and second plates to maintain the expandable inter-body fusion device in the fully expanded position supported at four spaced locations by the abutting flat surfaces of the ramps and respective sidewalls, and wherein the device is transitioned from the unexpanded position to the expanded position by longitudinally sliding the insert with respect to the first and second plates, thereby causing the at least one inclined surface of each of the ramps to exit the respective void and engage a portion of the sidewalls of the first and second plates to drive them apart.

17. The device of claim 16, wherein at least one longitudinal sidewall of at least one of the at least one longitudinal sidewalls of the first and second plates defines one of a groove, a recess, and a lip extending longitudinally along the at least one of the first and second plates, and wherein the insert defines a tongue extending in a longitudinal direction along the insert, the tongue being complementary to and mating with the one of the groove, recess and lip to allow expansion of the device.

18. The device of claim 16, wherein at least one longitudinal sidewall of at least one of the at least one longitudinal sidewalls of the first and second plates defines one of a groove, a recess, and a lip extending longitudinally along the at least one of the first and second plates, and wherein the insert defines a tongue extending in a longitudinal direction along the insert, the tongue being complementary to and mating with the one of the groove, recess and lip when the device is in the expanded position, to retain the first and second plates to the insert after expansion of the device.

19. An expandable inter-body fusion device for use in surgery comprising:
 a first plate having an upper bone contact surface, an opposed first inner surface and at least one longitudinal sidewall defining a lowermost sidewall surface contoured in a vertical direction;
 a second plate underlying at least a portion of the first plate, the second plate having a lower bone contact surface, an opposed second inner surface and at least one longitudinal sidewall defining an uppermost sidewall surface contoured in the vertical direction; and
 an insert positioned substantially between the first plate and the second plate, wherein the insert comprises a frame with a plurality of opposed continuous longitudinally extending lateral frame sides, wherein a continuous longitudinal rail protrudes laterally from a lateral surface of each of the longitudinally extending lateral frame sides to define upper and lower rail surfaces contoured in the vertical direction on opposing sides of each longitudinal rail and between the lowermost and uppermost sidewall surfaces, and wherein each longitudinal rail comprises a plurality of ramps including a pair of the plurality of ramps being longitudinally spaced on each opposed lateral extending side, each ramp of the plurality of ramps having at least one inclined surface and at least one substantially flat surface that define contours in the vertical direction of the upper and lower rail surfaces, wherein each longitudinal sidewall of the first plate substantially aligns with a respective longitudinal sidewall of the second plate to form a set of aligned sidewall surfaces defining a plurality of voids between the lowermost and uppermost sidewall surfaces, wherein the expandable inter-body fusion device is selectively adjustable between an unexpanded position, in which the device has an interior cavity having a first cavity size and each of the plurality of ramps of the insert is positioned substantially within a respective void of the plurality of voids between the aligned sidewall surfaces, and an expanded position, in which the interior cavity has a second cavity size greater than the first cavity size, and in a fully expanded position the at least one substantially flat surface of each of the ramps of the insert abuts at least a flat portion of the sidewall surfaces of the first and second plates to maintain the expandable inter-body fusion device in the fully expanded position supported at four spaced locations by the abutting flat surfaces of the ramps and respective sidewalls, and wherein the device is transitioned from the unexpanded position to the expanded position by longitudinally sliding the insert with respect to the first and second plates, thereby causing the at least one inclined surface of each of the ramps to engage with a portion of the sidewall surfaces of the first and second plates and drive them away from each other in the vertical direction.

20. The device of claim 19, wherein at least one longitudinal sidewall of at least one of the at least one longitudinal sidewalls of the first and second plates defines one of a groove, a recess, and a lip extending longitudinally along the at least one of the first and second plates, and wherein the insert defines a tongue extending in a longitudinal direction along the insert, the tongue being complementary to and mating with the one of the groove, recess and lip when the device is in the expanded position, to retain the first and second plates to the insert after expansion of the device.

* * * * *